United States Patent
Cales

(10) Patent No.: US 10,861,582 B2
(45) Date of Patent: Dec. 8, 2020

(54) NON-INVASIVE METHOD FOR ASSESSING LIVER FIBROSIS PROGRESSION

(71) Applicants: CENTRE HOSPITALIER UNIVERSITAIRE D'ANGERS, Angers (FR); UNIVERSITÉ D'ANGERS, Angers (FR)

(72) Inventor: Paul Cales, Avrille (FR)

(73) Assignees: CENTRE HOSPITALIER UNIVERSITAIRE D'ANGERS, Angers (FR); UNIVERSITÉ D'ANGERS, Angers (FR)

(*) Notice: Subject to any disclaimer, the term of this patent is extended or adjusted under 35 U.S.C. 154(b) by 581 days.

(21) Appl. No.: 15/608,287

(22) Filed: May 30, 2017

(65) Prior Publication Data

US 2017/0337322 A1    Nov. 23, 2017

Related U.S. Application Data

(63) Continuation-in-part of application No. 13/257,456, filed as application No. PCT/EP2010/053548 on Mar. 18, 2010, now abandoned.

(60) Provisional application No. 61/161,474, filed on Mar. 19, 2009.

(51) Int. Cl.
| | |
|---|---|
| *G16B 5/00* | (2019.01) |
| *G01N 33/68* | (2006.01) |
| *G16H 50/20* | (2018.01) |
| *G01N 33/576* | (2006.01) |
| *G16H 50/30* | (2018.01) |
| *G01N 33/574* | (2006.01) |
| *A61K 31/00* | (2006.01) |
| *G01N 33/50* | (2006.01) |
| *A61K 31/4178* | (2006.01) |
| *A61K 38/21* | (2006.01) |

(52) U.S. Cl.
CPC .............. *G16B 5/00* (2019.02); *A61K 31/00* (2013.01); *G01N 33/50* (2013.01); *G01N 33/576* (2013.01); *G01N 33/57438* (2013.01); *G01N 33/6893* (2013.01); *G16H 50/20* (2018.01); *G16H 50/30* (2018.01); *A61K 31/4178* (2013.01); *A61K 38/21* (2013.01); *G01N 2333/4713* (2013.01); *G01N 2333/495* (2013.01); *G01N 2333/78* (2013.01); *G01N 2400/40* (2013.01); *G01N 2800/085* (2013.01); *G01N 2800/52* (2013.01); *G01N 2800/60* (2013.01); *G01N 2800/7052* (2013.01)

(58) Field of Classification Search
CPC ...................................................... G16B 5/00
USPC ........................................................ 702/19
See application file for complete search history.

(56) References Cited

U.S. PATENT DOCUMENTS

| 2003/0175686 A1 | 9/2003 | Rose et al. |
| 2004/0053242 A1 | 3/2004 | Volker et al. |
| 2006/0014294 A1 | 1/2006 | Contreras et al. |
| 2007/0037224 A1 | 2/2007 | Hamer et al. |
| 2009/0143993 A1 | 6/2009 | Cales |
| 2010/0049029 A1 | 2/2010 | Li et al. |

FOREIGN PATENT DOCUMENTS

| EP | 1887362 | 2/2008 |
| WO | 2003064687 | 8/2003 |
| WO | 03/073822 | 9/2003 |
| WO | 2006/003654 | 1/2006 |
| WO | 2008152070 | 12/2008 |

OTHER PUBLICATIONS

Angulo et al., "The NAFLD fibrosis score: A noninvasive system that identities liver fibrosis in patients with NAFLD", Hepatology, 2007, 45(4):846-854.
Zarski et al., "Rate of natural disease progression in patients with chronic hepatitis C", Journal of Hepatology, 2003, 38:307-314.
Cales et al., Fibrosis progression under maintenance interferon in hepatitis C is better detected by blood test than liver morphometry, Journal of Viral Hepatitis, 2012, 19, e143-e153.
Baker et al., "Metalloproteinase Inhibitors: Biological Actions and Therapeutic Opportunities", Journal of Cell Science (2002) vol. 115, No. 19, pp. 3719-3727.
Bedossa et al., "Intraobserver and interobserver variations in liver biopsy interpretation in patients with chronic hepatitis C", Hepatology 1994; 20:15-20.
Bourliere et al., "Optimized stepwise combination algorithms of non-invasive liver fibrosis scores including Hepascore in hepatitis C virus patients", Alimentary Pharmacology &Therapeutics, 2008, 28(4): 458-467.
Cales et al., "Accuracy of liver fibrosis classifications provided by non-invasive tests", 2010, Journal of Hepatology, 52:S406.
Cales et al., FibroMeters: a family of blood tests for liver fibrosis, Gastroenterologie clinique et biologique 2008; 32:40-51.
Castera et al., "Prospective comparison of transient elastography, Fibrotest, APRI, and liver biopsy for the assessment of fibrosis in chronic hepatitis C", Gastroenterology 2005; 128:343-50.
Croquet et al., "Prothrombin index is an indirect marker of severe liver fibrosis", European Journal of Gastroenterology & Hepatology, 2002, 14(10): 1133-1141.
Friedrich-Rust et al., "Real-time elastography for noninvasive assessment of liver fibrosis in chronic viral hepatitis", Am. J. Roentgenol. 2007;188:758-764.

(Continued)

Primary Examiner — Jerry Lin
(74) Attorney, Agent, or Firm — Nixon & Vanderhye

(57) ABSTRACT

A method for implementing an adapted patient care for an individual suffering from liver fibrosis after assessing liver fibrosis progression in the individual, and thus determining whether the individual is a slow, medium or fast fibroser. Also, a method for treating an individual suffering from liver fibrosis and identified as a fast fibroser, which includes the steps of identifying the individual as a fast fibroser by assessing fibrosis progression and treating the individual by administering without delay at least one therapeutic agent for treating liver fibrosis, or for treating the underlying cause responsible for liver fibrosis, or both.

11 Claims, 17 Drawing Sheets

(56) References Cited

OTHER PUBLICATIONS

Halfon et al., Comparison of test performance profile for blood tests of liver fibrosis in chronic hepatitis C, Journal of Hepatology, 2007, 46(3):395-402.
Halfon et al. "Serum markers of non-invasive fibrosis in chronic hepatitis C virus infection", La revue de médecine interne, 2006, 27(10): 751-61.
Hubert JB, et al., "Natural history of serum HIV-1 RNA levels in 330 patients with a known date of infection." The SEROCO Study Group, Aids 2000; 14:123-131.
Leroy et al., "Prospective comparison of six non-invasive scores for the diagnosis of liver fibrosis in chronic hepatitis C", Journal of Hepatology, 2007, 46(5):775-82.
Maor et al., "Improving estimation of liver fibrosis using combination and newer noninvasive biomarker scoring systems in hepatitis C-infected haemophilia patients", Haemophilia, 2007, 13(6):722-9.
Michalak et al., "Repective roles of porto-septal fibrosis and centrilobular fibrosis in alcoholic liver disease", Journal of Pathology, 2003, 201(1):55-62.
Myers et al., "Biochemical markers of fibrosis in patients with chronic hepatitis C: a comparison with prothrombin time, platelet count, and age-platelet index", Digestive diseases and Sciences, 2003, 48(1):146-153.
Sebastiani et al., "Sequential algorithms combining non-invasive markers and biopsy for the assessment of liver fibrosis in chronic hepatitis B", World journal of gastroenterology, 2007, 13(4):525-531.
ISR of the corresponding PCT application (WO2010/106140).
Oberti et al., "Liver, Pancreas, and Biliary Tract", 1997; 113:1609-1616.
Poynard et al., "A Simple Biological Index for Detection of Alcoholic Liver Disease in Drinkers", Gastroenterology 1991; 100:1397-1402.
Naveau et al., "Alpha-2-Macroglobulin and Hepatic Fibrosis", Digestive Diseases and Sciences, 1994; 39:2426-2432.
Wai et al., "A Simple Noninvasive Index Can Predict Both Significant Fibrosis and Cirrhosis in Patients with Chronic Hepatitis C", Hepatology 2003; 38:518-526.
Adams et al., "Hepascore: An Accurate Validated Predictor of Liver Fibrosis in Chronic Hepatitis C Infection", Clinical Chemistry, 2005; 51:1867-1873.
Pilette et al., "Histopathological Evaluation of Liver Fibrosis: Quantitative Image Analysis vs. Semi-quantitative Scores", Journal of Hepatology 1998; 28:439-446.
Moal et al., "Fractal Dimension can Distinguish Models and Pharmacologic Changes in Liver Fibrosis in Rats", Hepatology, 2002; 36:840-849.
Cales et al., "A Novel Panel of Blood Markers to Assess the Degree of Liver Fibrosis", Hepatology 2005; 42:1373-1381.
Cales et al., "Evaluating the Accuracy and Increasing the Reliable Diagnosis Rate of Blood Tests for Liver Fibrosis in Chronic Hepatitis C", Liver International 2008; 28:1352-1362.
Marcellin et al., "Fibrosis and Disease Progression in Hepatitis C", Hepatology 2002, 36(5)—supplement 1:S47-S56.
Leroy et al., "Changes in Histological Lesions and Serum Fibrogenesis Markers in Chronic Hepatitis C Patients Non-responders to Interferon Alpha", Journal of Hepatology, 2001, 35(1):120-126.
Ghany et al., "Progression of Fibrosis in Chronic Hepatitis C", Gastroenterology, 2003, 124(1):97-104.
Meriden et al., "Histologic Predictors of Fibrosis Progression in Liver Allografts in Patients with Hepatitis C Virus Infection", Clinical Gastroenterology and Hepatology, 2010, 8(3):289-296.

Metavir F progression  Area of fibrosis progression

Metavir F progression

Population 1

Metavir F progression (MU/yr)

Area of fibrosis progression

Area of fibrosis progression (%/yr)

Population 2

Metavir F progression (MU/yr)

Area of fibrosis progression (%/yr)

Metavir F progression  Area of fibrosis progression
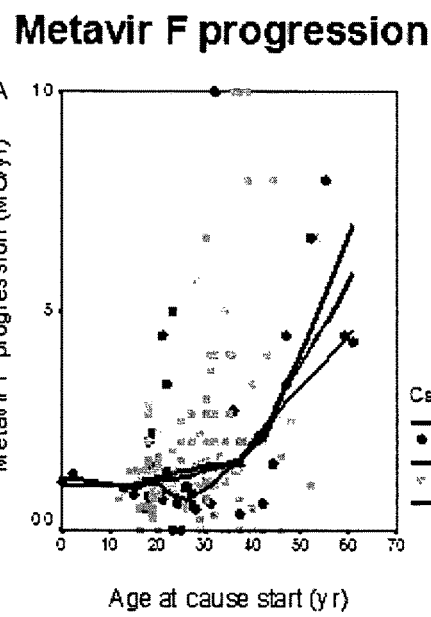
FIG. 12A (Population 1)
FIG. 12B (Population 1)
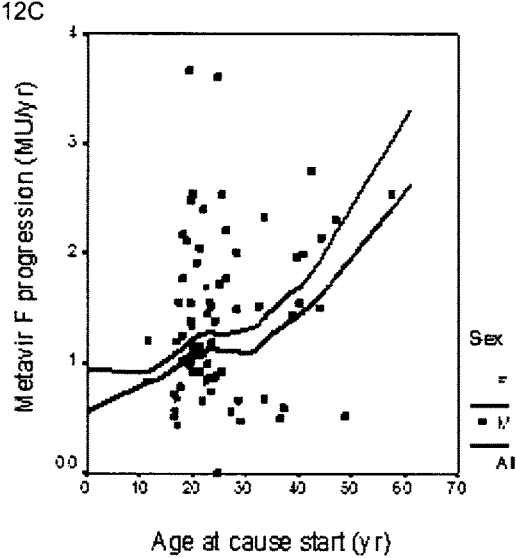
FIG. 12C (Population 2)
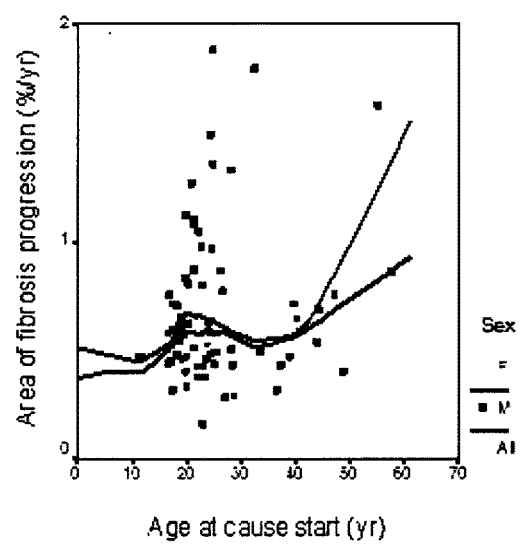
FIG. 12D (Population 2)

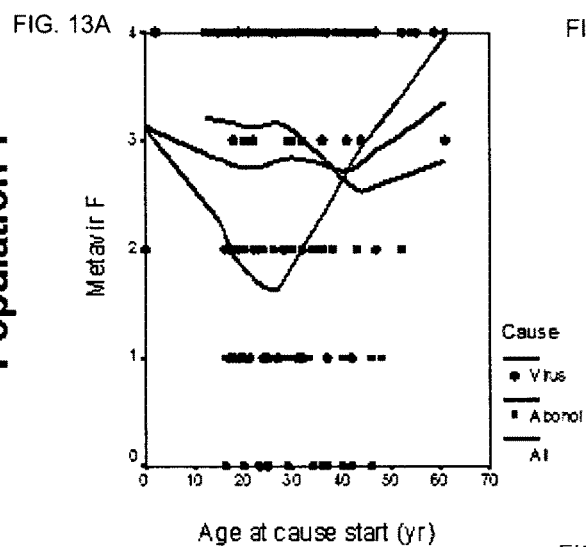
FIG. 13A
FIG. 13C
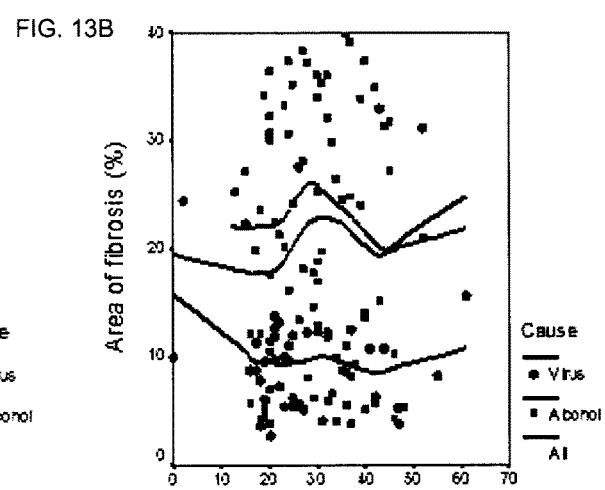
FIG. 13B
FIG. 13D

NON-INVASIVE METHOD FOR ASSESSING LIVER FIBROSIS PROGRESSION

FIELD OF INVENTION

The present invention relates to the field of hepatology and in particular to a non-invasive method for assessing the liver fibrosis progression and thus determining whether the individual is a slow, medium or fast fibroser, especially in alcohol or viral or metabolic chronic liver disease. The present invention further relates to a method for implementing an adapted patient care for an individual identified as a slow, medium or fast fibroser.

BACKGROUND OF INVENTION

Liver fibrosis refers to the accumulation of fibrous scar tissue in the liver. In order to diagnose liver fibrosis, various techniques can be used. One of these techniques is the liver needle biopsy (LNB), leading to a classification based on observation of lesions in the liver, particularly in the hepatic lobe. Indeed, one of the most commonly used classifications is the Metavir classification, which classifies liver fibrosis into five stages from F0 to F4. According to the Metavir classification, an F2 stage means that fibrosis is clinically significant, whereas a F4 stage corresponds to the ultimate stage, namely cirrhosis.

Other techniques, such as the measurement of the presence or the severity of fibrosis in an individual through a Fibrosis score (such as for example FibroMeter™), an area of fibrosis (AOF) score as well as quantitative image analysis can also be used alone or in combination with LNB or Metavir classification, in order to determine with more accuracy the extent of liver fibrosis in an individual.

However, if detecting the presence or the severity of liver fibrosis is of high importance, it is observed that progression rate of the fibrosis differs from an individual to another. Thus, the assessment of liver fibrosis progression would be a very important and useful tool in clinical practice for both prognostic and therapeutic reasons.

First, considering that liver fibrosis progression depends on various genetic and host factors, it may indeed be useful to determine ahead of time whether it is reasonable to expect that liver fibrosis will progress towards cirrhosis during the patient's lifetime and if it does, at what rate will this progression occur.

Second, assessing the progression rate of liver fibrosis can also be useful in order to help physicians decide whether or not to treat a patient or in order to help them monitor patients who are already following a treatment regimen. Until now, physicians relied mostly on fibrosis staging (ex. Metavir stage F2) in order to justify an antiviral treatment for chronic viral hepatitis. However, it would be very useful to know early on, such as for example but not limited to patients showing a stage F0 or F1, whether his liver fibrosis will evolve rapidly or not into clinically significant fibrosis or cirrhosis, in order for the physicians to anticipate the treatment.

Several documents have disclosed techniques developed in order to assess liver fibrosis progression. WO 03/064687 discloses a method for assessing a patient's risk of development and progression of liver cirrhosis, said method comprising the step of determining the patient's genotype or phenotype for a coagulation factor. WO 2006/003654 discloses methods and kits for determining the predisposition of an individual affected by chronic hepatitis C infection to develop a fast progression rate of liver fibrosis. This method essentially consists in determining the presence or absence, in the CYP2D6 locus of the individual, of at least one fast progression liver fibrosis associated genotype. EP 1887362A1 discloses a hepatic disease-evaluating method comprising a step of calculating an index indicating the degree of hepatic fibrosis from amino acid concentration data. Although, the aforementioned methods can assess liver fibrosis progression, they require sophisticated biological analysis which is not easily available in clinical practice.

Consequently, there is still a need for a low cost and easily available method which can evaluate the progression of fibrosis, said method being non-invasive, non-traumatizing, accurate and reliable, as well as simple to use.

SUMMARY

The present invention relates to a method for treating an individual suffering from liver fibrosis comprising:
  assessing the fibrosis progression in said individual to determine whether said individual is a slow fibroser, a medium fibroser or a fast fibroser, by
    measuring at least three markers in an individual, wherein said markers are measured in a blood sample obtained from the individual and are selected from the group consisting of α-2 macroglobulin, hyaluronic acid, gamma-glutamyl transpeptidase, bilirubin, platelet count, prothrombin index, aspartate amino-transferase, alanine amino-transferase, urea, glycemia, and ferritin; and/or said markers are clinical markers selected from weight, age and sex; and
    combining said at least four measured markers in a logistic or linear regression function, thereby determining a fibrosis level in the individual;
    calculating a ratio of said fibrosis level to cause duration, thereby obtaining a value-useful for assessing the liver fibrosis progression in the individual; and
  implementing an adapted patient care depending on whether the subject is a slow fibroser, a medium fibroser or a fast fibroser.

In one embodiment, fibrosis progression is assessed by measuring at two different times t1 and t2 the fibrosis levels FL(t1) and FL(t2); and calculating a ratio FL(t2)−FL(t1) to cause duration, wherein cause duration is defined as (t2−t1).

In one embodiment, the individual is determined to be a slow fibroser and the adapted patient care consists in monitoring said individual by assessing the fibrosis level at regular intervals.

In another embodiment, the individual is determined to be a medium fibroser and the adapted patient care consists in monitoring said individual by assessing the fibrosis level at regular intervals and delaying treatment until the individual is determined to suffer from clinically significant liver fibrosis.

In another embodiment, the individual is determined to be a fast fibroser and the adapted patient care consists in administering without delay at least one therapeutic agent or starting a complication screening program for applying early prophylactic or curative treatment.

In one embodiment, the at least one therapeutic agent is an antifibrotic agent selected from the group consisting of simtuzumab, GR-MD-02, stem cell transplantation (in particular MSC transplantation), *Phyllanthus urinaria*, Fuzheng Huayu, S-adenosyl-L-methionine, S-nitrosol-N-acetylcystein, silymarin, phosphatidylcholine, N-acetylcysteine, resveratrol, vitamin E, losartan, telmisartan, naltrexone, RF260330, sorafenib, gleevec, nilotinib, INT747, FG-3019, oltipraz, pirfenidone, halofuginone, polaorezin, gliotoxin, sulfasalazine, rimonabant and combinations thereof.

In one embodiment, the at least one therapeutic agent is for treating the underlying cause responsible for liver fibrosis, and/or ameliorating or alleviating the symptoms associated with the underlying cause responsible for liver fibrosis, including liver fibrosis.

In one embodiment, the underlying cause responsible for liver fibrosis is a viral infection and the at least one therapeutic agent is selected from the group consisting of interferon, peginterferon 2b (pegylated IFNalpha-2b), infliximab, ribavirin, boceprevir, telaprevir, simeprevir, sofosbuvir, daclatasvir, elbasvir, grazoprevir, velpatasvir, lamivudine, adefovir dipivoxil, entecavir, telbivudine, tenofovir, clevudine, ANA380, zadaxin, CMX 157, ARB-1467, ARB-1740, ALN-HBV, BB-HB-331, Lunar-HBV, ARO-HBV, Myrcludex B, GLS4, NVR 3-778, AIC 649, JNJ56136379, ABI-H0731, AB-423, REP 2139, REP 2165, GSK3228836, GSK33389404, RNaseH Inhibitor, GS 4774, INO-1800, HB-110, TG1050, HepTcell, TomegaVax HBV, RG7795, SB9200, EYP001, CPI 431-32 and combinations thereof.

In one embodiment, the underlying cause responsible for liver fibrosis is excessive alcohol consumption and the at least one therapeutic agent is selected from the group consisting of topiramate, disulfiram, naltrexone, acamprosate and baclofen.

In one embodiment, the underlying cause responsible for liver fibrosis is a non-alcoholic fatty liver disease (NAFLD) and the at least one therapeutic agent is selected from the group consisting of orlistat, metformin, pioglitazone, atorvastatin, ezetimine, vitamin E, sylimarine, pentoxyfylline, ARBs, EPL, EPA-E, multistrain biotic (*L. rhamnosus, L. bulgaricus*), simtuzumab, obeticholic acid, elafibranor (GFT505), DUR-928, GR-MD, 02, aramchol, RG-125, cenicriviroc CVC and combinations thereof.

The present invention further relates to a method for treating an individual suffering from liver fibrosis comprising:
  assessing the fibrosis progression in said individual to determine whether said individual is a slow fibroser, a medium fibroser or a fast fibroser, by
    measuring in a sample of the individual at least one variable or score further defined as:
      biological variables further defined as α-2 macroglobulin (α2M), Hyaluronic acid (HA), Apolipoprotein A1 (ApoA1), Type III procollagen N-terminal propeptide (P3P), γ-glutamyl transpeptidase (GGT), bilirubin, β-globulin, γ-globulin (GLB), Platelets (PLT), Prothrombin time (PT), Prothrombin index (PI), Aspartate aminotransferase (AST), Alanine aminotransferase (ALT), Urea, Sodium (NA), Glycemia, Triglycerides, Albumin (ALB), Alkaline phosphatase (ALP), Human cartilage glycoprotein 39 (YKL-40), Tissue inhibitor of matrix metalloproteinase 1 (TIMP-1), Matrix metalloproteinase 2 (MMP-2), Ferritin, TGFβ1, Laminin, βγ-block, Haptoglobin, C-Reactive protein (CRP), and/or cholesterol,
      complex biological variable;
      clinical variables further defined as age at first contact, age, cause duration, firm liver, splenomegaly, ascites, collateral circulation, cause of CLD, and/or esophageal varices (EV grade);
      score further defined as Metavir F stage, Area of fibrosis (AOF), fractal dimension, Fibrosis score, PGA score, PGAA score, Hepascore, Aspartate aminotransferase to platelet ratio index (APRI), and/or European Liver Fibrosis (ELF), and/or combinations thereof; and
    combining the selected variables in a mathematical function, further defined as a multiple linear regression function, a non-linear regression function, or simple mathematic function; and
  implementing an adapted patient care depending on whether the subject is a slow fibroser, a medium fibroser or a fast fibroser.

In one embodiment, the individual is determined to be a slow fibroser and the adapted patient care consists in monitoring said individual by assessing the fibrosis level at regular intervals.

In another embodiment, the individual is determined to be a medium fibroser and the adapted patient care consists in monitoring said individual by assessing the fibrosis level at regular intervals and delaying treatment until the individual is determined to suffer from clinically significant liver fibrosis.

In another embodiment, the individual is determined to be a fast fibroser and the adapted patient care consists in administering without delay at least one therapeutic agent or starting a complication screening program for applying early prophylactic or curative treatment.

In one embodiment, the at least one therapeutic agent is an antifibrotic agent selected from the group consisting of simtuzumab, GR-MD-02, stem cell transplantation (in particular MSC transplantation), *Phyllanthus urinaria*, Fuzheng Huayu, S-adenosyl-L-methionine, S-nitrosol-N-acetylcystein, silymarin, phosphatidylcholine, N-acetylcysteine, resveratrol, vitamin E, losartan, telmisartan, naltrexone, RF260330, sorafenib, gleevec, nilotinib, INT747, FG-3019, oltipraz, pirfenidone, halofuginone, polaorezin, gliotoxin, sulfasalazine, rimonabant and combinations thereof.

In one embodiment, the at least one therapeutic agent is for treating the underlying cause responsible for liver fibrosis, and/or ameliorating or alleviating the symptoms associated with the underlying cause responsible for liver fibrosis, including liver fibrosis.

In one embodiment, the underlying cause responsible for liver fibrosis is a viral infection and the at least one therapeutic agent is selected from the group consisting of interferon, peginterferon 2b (pegylated IFNalpha-2b), infliximab, ribavirin, boceprevir, telaprevir, simeprevir, sofosbuvir, daclatasvir, elbasvir, grazoprevir, velpatasvir, lamivudine, adefovir dipivoxil, entecavir, telbivudine, tenofovir, clevudine, ANA380, zadaxin, CMX 157, ARB-1467, ARB-1740, ALN-HBV, BB-HB-331, Lunar-HBV, ARO-HBV, Myrcludex B, GLS4, NVR 3-778, AIC 649, JNJ56136379, ABI-H0731, AB-423, REP 2139, REP 2165, GSK3228836, GSK33389404, RNaseH Inhibitor, GS 4774, INO-1800, HB-110, TG1050, HepTcell, TomegaVax HBV, RG7795, SB9200, EYP001, CPI 431-32 and combinations thereof.

In one embodiment, the underlying cause responsible for liver fibrosis is excessive alcohol consumption and the at least one therapeutic agent is selected from the group consisting of topiramate, disulfiram, naltrexone, acamprosate and baclofen.

In one embodiment, the underlying cause responsible for liver fibrosis is a non-alcoholic fatty liver disease (NAFLD) and the at least one therapeutic agent is selected from the group consisting of orlistat, metformin, pioglitazone, atorvastatin, ezetimine, vitamin E, sylimarine, pentoxyfylline, ARBs, EPL, EPA-E, multistrain biotic (*L. rhamnosus, L. bulgaricus*), simtuzumab, obeticholic acid, elafibranor (GFT505), DUR-928, GR-MD, 02, aramchol, RG-125, ceni-criviroc CVC and combinations thereof.

Another object of the invention is a method for treating an individual suffering from liver fibrosis and identified as a fast fibroser, said method comprising:
- identifying an individual suffering from liver fibrosis as a fast fibroser by
  - assessing fibrosis progression in the individual, measuring at least three markers in an individual, wherein said markers are measured in a blood sample obtained from the individual and are selected from the group consisting of α-2 macroglobulin, hyaluronic acid, gamma-glutamyl transpeptidase, bilirubin, platelet count, prothrombin index, aspartate amino-transferase, alanine amino-transferase, urea, glycemia, and ferritin; and/or said markers are clinical markers selected from weight, age and sex; and
  - combining said at least four measured markers in a logistic or linear regression function, thereby determining a fibrosis level in the individual;
  - calculating a ratio of said fibrosis level to cause duration, thereby obtaining a value-useful for assessing the liver fibrosis progression in the individual; and
- treating the individual suffering from liver fibrosis identified as a fast fibroser administering without delay at least one therapeutic agent, wherein said therapeutic agent is for treating liver fibrosis, or for treating the underlying cause responsible for liver fibrosis, or both.

DEFINITIONS

For the purpose of the present invention,

"About" preceding a figure means plus or minus 10% of the value of said figure.

"Score" is a combination of markers (or variables) aimed at predicting a clinical event or a lesion such as fibrosis degree. Usually, and especially when using the binary logistic regression, the score ranges from 0 (0% risk) to 1 (100% risk), i.e. the probability of the diagnostic target. When the score relies on multiple linear regression, the score produces a result in the same units as the diagnostic target. In the present invention, the main scores are derived from multiple linear regression and measure a progression rate of fibrosis, i.e. expressed as a fibrosis unit per time unit.

"Progression" means the evolution of the fibrosis level over time.

"Regularly" means at regular intervals, such as for example, every 10-day, every month, or every year, etc.

"Sample" means a biological fluid of an individual, such as for example blood, serum, plasma, urine or saliva of an individual.

"Non-invasive" means that no tissue is taken from the body of an individual (blood is not considered as a tissue).

"Individual" means a woman, a man or an animal, young or old, healthy or susceptible of being affected or clearly affected by a hepatic pathology, such as a liver fibrosis of viral origin, of alcohol origin, a chronic liver steatosis or by any other pathology.

"Cause" means the risk factor that induces the lesions and the ensuing pathology.

"Cause duration" is the time between the age when the cause started ("start age") and the age at inclusion when fibrosis level was measured ("inclusion age").

"Fibrosis level" is reflected by a Fibrosis Score, AOF or fractal dimension, preferably fibrosis level is a fibrosis score or an AOF score or a fractal dimension score.

"FibroMeter" may refer to a fibrosis score or to a AOF score.

"Fibroser" in the present invention refers to an individual suffering from liver fibrosis. Left untreated, liver fibrosis will worsen over time and ultimately lead to the development of cirrhosis. Cirrhosis can be associated with severe and sometimes life threatening complications, such as ascites, spontaneous bacterial peritonitis, hepatic encephalopathy, portal hypertension, variceal bleeding, hepatorenal syndrome and liver cancer.

"Slow fibroser" refers to an individual suffering from liver fibrosis who, in the absence of treatment, is at little if no risk for developing a cirrhosis, or is at very-long term risk of developing a cirrhosis. For example, in one embodiment, in the absence of treatment, a slow fibroser is likely to develop cirrhosis after more than 40 years, 45 years, 50 years or more following the initial detection of liver fibrosis. Thus, in one embodiment, in the absence of treatment, a slow fibroser will not have developed cirrhosis by the age of 50 years, 55 years, 60 years or 65 years. Accordingly, a slow fibroser should be monitored but does not require treatment.

"Medium fibroser" or "Intermediate fibroser" refers to an individual suffering from liver fibrosis who, in the absence of treatment, is at long-term risk for developing a cirrhosis. According to the present invention, in the absence of treatment, a medium fibroser or intermediate fibroser is likely to develop cirrhosis after 20 years, 25 years, 30 years, 35 years, 40 years following the initial detection of liver fibrosis. Thus, in one embodiment, in the absence of treatment, a medium fibroser or intermediate fibroser is likely to develop cirrhosis by the age of 50 years, 55 years, 60 years or 65 years. Accordingly, a medium fibroser or intermediate fibroser should be monitored to determine the time at which administration of treatment will be required.

"Fast fibroser" refers to an individual suffering from liver fibrosis who, in the absence of treatment, is at short-term risk for developing cirrhosis. According to the present invention, in the absence of treatment, a fast fibroser is likely to develop cirrhosis after 1 year, 2 years, 3 years, 4 years, 5 years, 10 years or 15 years following the initial detection of liver fibrosis. Thus, in one embodiment, in the absence of treatment, a fast fibroser is likely to develop cirrhosis before the age of 45 years, 50 years, 55 years, 60 years or 65 years. Accordingly, a fast fibroser should be treated without delay. In other words, treatment should be started as soon as a fast fibroser has been identified as such.

DETAILED DESCRIPTION

The present invention proposes a solution to the technical issue of assessing the progression rate of fibrosis in all and any condition or disease involving fibrosis. This invention results in a very accurate diagnosis of fibrosis progression and in the ability of distinguishing slow, medium and fast fibrosers.

In a preferred embodiment, the condition or disease is alcohol or viral chronic liver disease (CLD). According to another embodiment, in order to assess the progression rate of fibrosis, the progression rate of area of fibrosis (AOF) is assessed.

According to a first embodiment of the invention, the liver fibrosis progression is assessed by calculating the ratio fibrosis level/cause duration. According to a preferred embodiment, fibrosis level is measured by a non-invasive method. Advantageously, the fibrosis level is a fibrosis score, preferably FibroMeter™, AOF score or fractal dimension score.

According to a second embodiment of the invention, the liver fibrosis progression is assessed by measuring, at two different intervals $t_1$ and $t_2$, the fibrosis levels $FL(t_1)$ and $FL(t_2)$ and calculating the ratio $FL(t_2)-FL(t_1)$ to $(t_2-t_1)$.

According to the invention, "$t_1$": is the time at which a first measure is performed in an individual and a first fibrosis level $FL(t_1)$ is determined; "$t_2$": is the time at which a second measure is performed in the same individual and a second fibrosis level $FL(t_2)$ is determined; "$t_2-t_1$" is a period of time of at least 10 days; in an embodiment, $t_2-t_1$ is a period of 1 to 6 months; in another embodiment, $t_2-t_1$ is a period of 1 month, 2 months, 3 months, 4 months, 5 months, 6 months, 7 months, 8 months, 9 months, 10 months, 11 months, 12 months, 13 months, 14 months, 15 months, 16 months, 17 months, or 18 months; in another embodiment, t2–t1 is a period of 1 year, 2 years, 3 years, 4 years or 5 years.

Advantageously, the fibrosis level is a fibrosis score, AOF score or fractal dimension score.

According to this invention, "Fibrosis Score" is a score obtained by measuring in a sample of an individual and combining in a logistic or linear regression function at least three, preferably 6 to 8, markers selected in the group consisting of α-2 macroglobulin (A2M), hyaluronic acid (HA or hyaluronate), apoliprotein A1 (ApoA1), N-terminal propeptide of type III procollagen (P3P), gamma-glutamyl transpeptidase (GGT), bilirubin, gamma-globulins (GLB), platelet count (PLT), prothrombin index (PI), aspartate aminotransferase (AST), alanine aminotransferase (ALT), urea, sodium (NA), glycemia (GLY) also referred to as glucose (or blood glucose level), triglycerides (TG), albumin (ALB), alkaline phosphatases (ALP), human cartilage glycoprotein 39 (YKL-40), tissue inhibitor of matrix metalloproteinase 1 (TIMP-1), matrix metalloproteinase 2 (MMP-2), ferritin, weight, age and sex. Preferably, the Fibrosis Score is measured by combining the levels of at least three markers selected from the group consisting of glycemia (GLY) also referred to as glucose (or blood glucose level), aspartate aminotransferase (AST), alanine aminotransferase (ALT), ferritin, hyaluronic acid (HA), triglycerides (TG), prothrombin index (PI) gamma-globulins (GLB), platelet count (PLT), weight, age and sex. More preferably, the Fibrosis score is established by combining in a binary linear regression function, the levels of four to eight markers, preferably selected from the group consisting of Alpha2 macroglobulin (A2M), hyaluronic acid or hyaluronate (AH), Prothrombin index (PI) Platelets (PLQ), ASAT, Urea, GGT, Age and Sex. According to a preferred embodiment, the Fibrosis score is a FibroMeter™ or Fibrotest™ or Fibrospect™ or Hepascore.

According to a specific embodiment, the markers of the score may be selected depending on the fact that the liver condition is of viral or alcoholic origin.

"Area Of Fibrosis" may be determined by image analysis, or by a non invasive method wherein a score is obtained by measuring in a sample of said patient and then combining in a logistic or linear regression function, preferably in a multiple linear regression function, at least two, preferably 3, more preferably 6 to 8 variables selected from the group consisting of α-2 macroglobulin (A2M), hyaluronic acid (HA or hyaluronate), apoliprotein A1 (ApoA1), procollagen Type III-N-terminal propeptide (P3P), gamma-glutamyl transpeptidase (GGT), bilirubin, gamma-globulins (GLB), platelet count (PLT), prothrombin index (PI), aspartate aminotransferase (AST), alanine aminotransferase (ALT), urea, sodium (NA), glycemia also referred to as glucose (or blood glucose level), triglycerides, albumin (ALB), alkaline phosphatases (ALP), human cartilage glycoprotein 39 (YKL-40), tissue inhibitor of matrix metalloproteinase 1 (TIMP-1), matrix metalloproteinase 2 (MMP-2), ferritin, age, weight, body mass index.

"Fractal dimension" reflects the liver architecture and may be obtained by image analysis or by a non invasive method wherein a score is obtained by measuring in a sample of an individual and combining in a logistic or linear regression function (preferably a multiple linear regression function) at least three, preferably 4 markers selected in the group comprising or consisting of α-2 macroglobulin (A2M), albumin (ALB), Prothrombin index (PI), hyaluronic acid (HA or hyaluronate), alanine aminotransferase (ALAT), aspartate aminotransferase (ASAT) and age.

According to a preferred embodiment of the invention, the fibrosis level is selected from the scores set forth in the table below:

| Fibrosis | FibroMeter | | | | | |
| --- | --- | --- | --- | --- | --- | --- |
| | Virus | | Alcohol | | NAFLD | |
| | Score | Area | Score | Area | Score | Area |
| Age | x | | x | | x | |
| Sex | x | | | | | |
| Body weight | | | | | x | |
| alpha2 macroglobulin | x | x | x | x | | |
| Hyaluronate | x | x | x | x | | |
| Prothrombin index | x | | x | x | | x |
| Platelet | x | x | | x | x | x |
| AST | x | | | | x | x |
| Urea | x | x | | | | |
| GGT | x | x | | | | |
| Bilirubin | | x | | | | |
| ALT | | | | | x | x |
| Ferritin | | | | | x | |
| Glycemia | | | | | x | x |

According to the invention, the FibroMeter fibrosis score is a score obtained by combining in a logistic or linear regression function the following markers:
  when the underlying cause responsible for liver fibrosis is a viral infection: age, sex, α-2 macroglobulin (A2M), hyaluronate (HA), prothrombin index (PI), platelet (PLT), aspartate aminotransferase (AST), urea and gamma-glutamyl transpeptidase (GGT);
  when the underlying cause responsible for liver fibrosis is excessive alcohol consumption: age, α-2 macroglobulin (A2M), hyaluronate (HA) and prothrombin index (PI);
  when the underlying cause responsible for liver fibrosis is non-alcoholic fatty liver disease (NAFLD): age, body weight, platelet (PLT), aspartate aminotransferase (AST), alanine aminotransferase (ALT), ferritin and glycemia.

According to the invention, the FibroMeter Area of Fibrosis (AOF) score is a score obtained by combining in a logistic or linear regression function the following markers:
  when the underlying cause responsible for liver fibrosis is a viral infection: α-2 macroglobulin (A2M), hyaluronate (HA), platelet (PLT), urea, gamma-glutamyl transpeptidase (GGT) and bilirubin;
  when the underlying cause responsible for liver fibrosis is excessive alcohol consumption: α-2 macroglobulin (A2M), hyaluronate (HA), prothrombin index (PI) and platelet (PLT);
  when the underlying cause responsible for liver fibrosis is non-alcoholic fatty liver disease (NAFLD): prothrombin index (PI), platelet (PLT), aspartate aminotransferase (AST), alanine aminotransferase (ALT) and glycemia.

According to an embodiment of the invention, the fibrosis score is a FibroMeter.

In one embodiment, the FibroMeter is a blood test based on alpha-2 macroglobulin (A2M), hyaluronic acid (or hyaluronate), prothrombin index, platelets, aspartate aminotransferase (AST), urea, gamma-glutamyl transpeptidase (GGT), alanine aminotransferase (ALT), ferritin, glucose, age, sex and optionally weight.

In one embodiment, the underlying cause responsible for liver fibrosis is a viral infection and the FibroMeter, also referred to as FibroMeter$^{V1G}$, is based on alpha-2 macroglobulin (A2M), hyaluronic acid (or hyaluronate), prothrombin index, platelets, aspartate aminotransferase (AST), urea and age. In another embodiment, the underlying cause responsible for liver fibrosis is a viral infection and the FibroMeter, also referred to as FibroMeter$^{V2G}$, is based on alpha-2 macroglobulin (A2M), hyaluronic acid (or hyaluronate), prothrombin index, platelets, aspartate aminotransferase (AST), urea, age and sex. In yet another embodiment, the underlying cause responsible for liver fibrosis is a viral infection and the FibroMeter, also referred to as FibroMeter$^{V3G}$, is based on alpha-2 macroglobulin (A2M), gamma-glutamyl transpeptidase (GGT), prothrombin index, platelets, aspartate aminotransferase (AST), urea, age and sex.

In one embodiment, the underlying cause responsible for liver fibrosis is excessive alcohol consumption and the FibroMeter, also referred to as FibroMeter$^{A1G}$, is based on alpha-2 macroglobulin (A2M), hyaluronic acid (or hyaluronate), prothrombin index and age. In another embodiment, the underlying cause responsible for liver fibrosis is excessive alcohol consumption and the FibroMeter, also referred to as FibroMeter$^{A2G}$ or FibroMeter$^{ALD}$, is based on alpha-2 macroglobulin, hyaluronic acid (or hyaluronate), and prothrombin index.

In one embodiment, the underlying cause responsible for liver fibrosis is non-alcoholic fatty liver disease (NAFLD) and the FibroMeter, also referred to as FibroMeter$^{NAFLD}$, is based on platelets, aspartate aminotransferase (AST), aminotransferase (ALT), ferritin, glucose, age and weight. In another embodiment, the underlying cause responsible for liver fibrosis is non-alcoholic fatty liver disease (NAFLD) and the FibroMeter, also referred to as QuantiMeter$^{NAFLD}$, is based on prothrombin index (PI), platelet (PLT), aspartate aminotransferase (AST), alanine aminotransferase (ALT), glycemia and hyaluronic acid (or hyaluronate).

In one embodiment, the FibroMeter, also referred to as FibroMeter$^{VCTE2G}$, is based on alpha-2 macroglobulin (A2M), hyaluronic acid (or hyaluronate), prothrombin index, platelets, aspartate aminotransferase (AST), age, sex and liver stiffness measurement. In another embodiment, the FibroMeter, also referred to as FibroMeter$^{VCTE3G}$, is based on alpha-2 macroglobulin (A2M), gamma-glutamyl transpeptidase (GGT), prothrombin index, platelets, aspartate aminotransferase (AST), age, sex and liver stiffness measurement.

According to the invention, liver stiffness measurement (LSM), sometimes also called liver stiffness evaluation (LSE) is preferably measured by Vibration Controlled Transient Elastography or VCTE (also known as Fibroscan™, Paris, France). In one embodiment, the measure by VCTE is performed with the M probe. Preferably, examination conditions are those recommended by the manufacturer, with the objective of obtaining at least 3 and preferably 10 valid measurements. Results may be expressed as the median (kilopascals) of all valid measurements, and as IQR (interquartile range) or as the ratio (IQR/median).

This invention also relates to a non-invasive method for assessing whether or not an individual is a fast fibroser, i.e. for assessing whether or not an individual is at short-term risk for developing cirrhosis. The method of the invention includes measuring the liver progression of said individual by using a non-invasive method as described hereinabove, preferably by calculating FL/cause duration and/or FL(t2)−FL(t$_1$)/t$_2$−t$_1$, wherein FL preferably is a fibrosis score, an AOF score or a fractal dimension score. According to one embodiment of the invention, the fast fibroser may be identified with reference to statistical data as having an increased AOF, younger inclusion age and older start age (or cause duration replacing the two previous variables) by stepwise binary logistic regression. According to the Applicant experiments, the diagnostic accuracy seems to be of 100.0% by stepwise binary logistic regression.

This invention also relates to a non-invasive method for assessing if an individual is a slow, medium or fast fibroser. In one embodiment, the method of the invention rely on the previous use of discriminant analyses to sort the individuals of a reference population suffering from liver fibrosis in three categories, i.e. slow, medium and fast fibrosers, on the basis of their fibrosis progression rate. In one embodiment, the method of the invention comprises, first assessing the fibrosis progression of an individual as described hereinabove above, and then, identifying the individual as belonging to the slow, medium, fast or fibroser category as previously determined using the reference population by statistical analysis. In the Example 2 below, cut-offs were 0.58 and 1.36%/yr distinguishing slow (52.5%), medium (34.5%) and fast (12.9%) fibrosers where the median AOF progression was: 0.42±0.10, 0.81±0.21 and 2.43±0.81%/yr (p<10$^{-3}$), respectively. Fibrosers, preferably defined by AOF progression, are in agreement with the median Fibrosis progression: 0.09±0.06, 0.15±0.06 and 0.43±0.18 MU/yr (p<10$^{-3}$), corresponding respectively to slow, medium and fast fibrosers. According to a preferred embodiment, the non-invasive method here above described to assess the fibrosis progression of an individual is FL/cause duration or FL(t2)−FL(t1)/t2−t1, wherein FL (fibrosis level) preferably is AOF score, or a FibroMeter score.

According to a fourth embodiment of the invention, liver fibrosis progression is assessed by a score.

According to a first object, the invention relates to a non-invasive method for assessing liver fibrosis progression in an individual, said method comprising the steps of:

a) measuring in a sample of said individual, at least one, preferably at least two, more preferably at least three, even more preferably six to eight variables selected from the group consisting of
biological variables chosen among α-2 macroglobulin (α2M), Hyaluronic acid (HA), Apolipoprotein A1 (ApoA1), Type III procollagen N-terminal propeptide (P3P), γ-glutamyl transpeptidase (GGT), Bilirubin, γ-globulin (GLB), Platelets (PLT), Prothrombin time (PT), Prothrombin index (PI), Aspartate aminotransferase (AST), Alanine aminotransferase (ALT), Urea, Sodium (NA), Glycemia also referred to as glucose (or blood glucose level), Triglycerides, Albumin (ALB), Alkaline phosphatase (ALP), Human cartilage glycoprotein 39 (YKL-40), Tissue inhibitor of matrix metalloproteinase 1 (TIMP-1), Matrix metalloproteinase 2 (MMP-2), Ferritin, TGFβ1, Laminin, βγ-block, Haptoglobin, C-Reactive protein (CRP) or Cholesterol, preferably chosen among α-2 macroglobulin (α2M), Hyaluronic acid (HA), Type III procollagen N-terminal propeptide (P3P), γ-glutamyl transpeptidase (GGT), β-globulin, Platelets (PLT), Prothrombin time (PT), Prothrombin index (PI), Aspartate aminotransferase (AST), Alanine aminotransferase (ALT), Glycemia also referred to as glucose (or blood glucose level), Triglycerides, Tissue inhibitor of matrix metalloproteinase 1 (TIMP-1) or βγ-block, more preferably chosen among α-2 macroglobulin (α2M), Hyaluronic acid (HA), Type III procollagen N-terminal propeptide (P3P), γ-glutamyl transpeptidase (GGT), β-globulin, Prothrombin index (PI) or βγ-block, complex biological variables such as for example AST/ALT, clinical variables chosen among age at 1st contact "start age", age, cause duration, sex, firm liver, splenomegaly, ascites, collateral circulation, cause of CLD or Oesophageal varices (EV grade), preferably chosen among age at 1st contact, age, cause duration, sex or cause of CLD, scores chosen among Metavir F stage, Area of fibrosis (AOF), Fibrosis score (such as for example FibroMeter™, Fibrotest™, Fibrospect™, Fibroscan™ preferably FibroMeter™), PGA score, PGAA score, Hepascore, Aspartate-aminotransferase to platelet ratio index (APRI) or European Liver Fibrosis (ELF), and any combination thereof, b) combining the selected variables in a mathematical function selected from the group consisting of multiple linear regression function, a non-linear regression function, or simple mathematic function such as arithmetic operation, for example division.

According to a preferred embodiment, the method includes combining at least two biological variables or at least two scores, and at least one clinical variable selected from cause duration, especially Chronic Liver Disease duration and age at first contact with cause (also named "start age"). Preferably, the at least one clinical variable is cause duration. Alternatively, the at least one clinical variable is age at first contact with cause ("start age"). Preferably, the method includes two clinical variables. According to a preferred embodiment, the two clinical variables are cause duration and start age. Advantageously, the at least one score is selected from the group consisting of Area of Fibrosis (AOF) and/or the Fibrosis Score and/or Fractal dimension.

According to a first embodiment of the invention, the liver fibrosis progression is assessed by measuring Metavir F progression, said Metavir F progression being established by measuring the following:

biological variables chosen among Type III procollagen N-terminal propeptide (P3P), Hyaluronic acid (HA), Prothrombin index (PI), γ-glutamyl transpeptidase (GGT) or βγ-block, the complex biological variable AST/ALT, clinical variables chosen among Age at 1st contact, Cause duration, scores chosen among Metavir F stage, Area of fibrosis (AOF), PGA score, PGAA score or FibroMeter™, and any combination thereof, and combining the selected variables in a mathematical function selected from the group consisting of multiple linear regression function, a non-linear regression function, or simple mathematic function such as arithmetic operation, for example division.

In this embodiment, preferably, the variable sex is not selected.

In this embodiment, according to a first object, the variables are:

the biological variable Prothrombin index (PI),
the complex biological variable AST/ALT,
the clinical variable Cause duration,
the score Metavir F stage, and
any combination thereof.

In this embodiment, according to a second object, the variables are:

the complex biological variable AST/ALT,
clinical variables chosen among Cause duration or Age at 1st contact,
the score FibroMeter™, and
any combination thereof.

In this embodiment, according to a third object, the variables are:

the complex biological variable AST/ALT,
clinical variables chosen among Cause duration, and
any combination thereof.

According to a second embodiment of the invention, the liver fibrosis progression is assessed by measuring the area of fibrosis (AOF) progression, said AOF progression being established by measuring the following:

biological variables chosen among α-2 macroglobulin (α2M), Hyaluronic acid (HA), Prothrombin index (PI) or βγ-block, the complex biological variable AST/ALT, clinical variables chosen among age at 1st contact, age, cause duration, sex, firm liver, splenomegaly, ascites, collateral circulation or cause of CLD, scores chosen among Metavir F stage, Area of fibrosis (AOF), FibroMeter™, PGA score or PGAA score, and any combination thereof, and combining the selected variables in a mathematical function selected from the group consisting of multiple linear regression function, a non-linear regression function, or simple mathematic function such as arithmetic operation, for example division.

In this second embodiment, according to a first object, the variables are:

the biological variable β-globulins,
the complex biological variable AST/ALT,
the clinical variable Cause duration,
the score Area of fibrosis (AOF), and
any combination thereof.

In this second embodiment, according to a second object, the variables are:

the biological variable β-globulins,
the complex biological variable AST/ALT,
the clinical variable Cause duration,
the score Metavir F stage, and
any combination thereof.

In this second embodiment, according to a third object, the variables are:

biological variables chosen among β-globulins or Prothrombin index (PI),
the complex biological variable AST/ALT,
clinical variables chosen among Cause duration or Firm liver, and
any combination thereof.

In this second embodiment, according to a fourth object, the variables are:

biological variables chosen among β-globulins or Prothrombin index (PI),
the complex biological variable AST/ALT, clinical variables chosen among Age at 1st contact, Cause duration or Firm liver, and
any combination thereof.

In this second embodiment, according to a fourth object, the variables are:
biological variables chosen among β-globulins or α-2 macroglobulin (α2M),
the complex biological variable AST/ALT,
clinical variables chosen among Age at 1st contact or Cause duration, and
any combination thereof.

According to a particular embodiment, the non-invasive method of the invention includes at least two fibrosis scores, measured at regular intervals, such as for example, every 10-day, every month, or every year. In one embodiment, the non-invasive method of the invention includes measuring the fibrosis level (FL) of an individual, as described hereinabove, at regular intervals. In one embodiment, the fibrosis level (FL) is measured every 15 day or every 30 day. In one embodiment, the fibrosis level (FL) is measured every month, every 3 months, every 6 months, every 9 months, every 12 months or every 18 months. In one embodiment, the fibrosis level (FL) is measured every year, every two years, every three years, every four years or every five years.

According to the invention, the individual may be at risk of suffering or is suffering from a condition selected from the group consisting of a chronic liver disease, a hepatitis viral infection, a hepatotoxicity, a liver cancer, a non-alcoholic fatty liver disease (NAFLD), an autoimmune disease, a metabolic liver disease and a disease with secondary involvement of the liver.

Hepatitis viral infection may be caused by a virus selected from the group consisting of hepatitis C virus, hepatitis B virus and hepatitis D virus. Hepatotoxicity may be alcohol induced hepatotoxicity and/or drug-induced hepatotoxicity (i.e. any xenobiotic like alcohol or drug). According to the invention, autoimmune disease is selected from the group consisting of autoimmune hepatitis (AIH), primary biliary cirrhosis (PBC) and primary sclerosing cholangitis (PSC). Metabolic liver disease may be selected from the group consisting of Hemochromatosis, Wilson's disease and alpha 1 anti-trypsin. Secondary involvement of the liver may be celiac disease or amyloidosis.

Another object of the invention is a method for implementing an adapted patient care for an individual suffering from liver fibrosis comprising:
assessing the fibrosis progression in said individual to determine whether said individual is a slow fibroser, a medium fibroser or a fast fibroser as described hereinabove, and
implementing an adapted patient care depending on whether the subject is a slow fibroser, a medium fibroser or a fast fibroser.

In one embodiment, the adapted patient care allows preventing cirrhosis and/or complications thereof in the patient.

In another embodiment, the adapted patient care allows treating fibrosis and/or cirrhosis and/or complications thereof. Examples of adapted patient cares thus include, without limitation, administration of a therapeutic agent (including, without limitation, antifibrotic drugs and antiviral drugs), liver transplantation or removal of the underlying cause of liver fibrosis (excessive body weight, alcohol or drug consumption and the like).

In one embodiment, the adapted patient care correspond to a complication screening program (preferably a program of screening of cirrhosis complications), thereby applying as early as possible a prophylactic and/or curative treatment to the subject.

According to one embodiment, fibrosis progression is assessed by calculating the ratio fibrosis level/cause duration as described hereinabove. According to another embodiment, fibrosis progression is assessed by measuring, at two different intervals $t_1$ and $t_2$, the fibrosis levels $FL(t_1)$ and $FL(t_2)$ and calculating the ratio $FL(t_2)-FL(t_1)$ to cause duration, wherein cause duration is defined as $(t_2-t_1)$.

In one embodiment, fibrosis progression is assessed by:
measuring at least three markers in an individual, wherein said markers are measured in a blood sample obtained from the individual and are selected from the group consisting of α-2 macroglobulin, hyaluronic acid, gamma-glutamyl transpeptidase, bilirubin, platelet count, prothrombin index, aspartate amino-transferase, alanine amino-transferase, urea, glycemia, and ferritin; and/or said markers are clinical markers selected from weight, age and sex;
combining said at least four measured markers in a logistic or linear regression function, thereby determining a fibrosis level in the individual;
calculating a ratio of said fibrosis level to cause duration, thereby obtaining a value useful for assessing the liver fibrosis progression in the individual.

Thus, in one embodiment, the fibrosis level (FL) is obtained by:
measuring at least three markers in an individual, wherein said markers are measured in a blood sample obtained from the individual and are selected from the group consisting of α-2 macroglobulin, hyaluronic acid, gamma-glutamyl transpeptidase, bilirubin, platelet count, prothrombin index, aspartate amino-transferase, alanine amino-transferase, urea, glycemia, and ferritin; and/or said markers are clinical markers selected from weight, age and sex;
combining said at least four measured markers in a logistic or linear regression function, thereby determining a fibrosis level in the individual In one embodiment, the fibrosis level (FL) is a fibrosis score or an AOF score as described hereinabove. In one embodiment, the fibrosis level (FL) is a FibroMeter score. In one embodiment, the fibrosis level (FL) is a FibroMeter score selected from the group consisting of FibroMeter$^{V1G}$, FibroMeter$^{V2G}$, FibroMeter$^{V3G}$, FibroMeter$^{41G}$, FibroMeter$^{42G}$, FibroMeter$^{NAFLD}$, FibroMeter$^{VCTE2G}$, FibroMeter$^{VCTE3G}$ and QuantiMeter$^{NAFLD}$.

According to another embodiment, fibrosis progression is assessed by determining a score as described hereinabove.

According to the present invention, fibrosis progression is directly linked with the risk of developing cirrhosis, i.e. the ultimate stage of liver fibrosis. Cirrhosis may lead to complications and eventually to death. Complications of cirrhosis include ascites, spontaneous bacterial peritonitis, hepatic encephalopathy, portal hypertension, variceal bleeding, hepatorenal syndrome and liver cancer.

According to the present invention, a slow fibroser is an individual suffering from liver fibrosis with a very low liver fibrosis progression rate. In a slow fibroser, liver fibrosis will not evolve in cirrhosis. In other words, a slow fibroser is not at risk for developing cirrhosis and any of the ensuing associated complications.

In one embodiment, a slow fibroser has an AOF fibrosis progression of less than about 0.30, 0.40, 0.50, 0.60 or 0.70%/year. In one embodiment, a slow fibroser has a AOF fibrosis progression of less than about 0.45, 0.50, 0.55, 0.60, 0.65 or 0.70%/year. In one embodiment, a slow fibroser has a AOF fibrosis progression of less than about 0.48, 0.50, 0.52, 0.54, 0.56, 0.58, 0.60, 0.62, 0.64, 0.66, 0.68 or 0.70%/year. In one embodiment, a slow fibroser has a AOF fibrosis progression of less than 0.58%/year.

In one embodiment, a slow fibroser has a fibrosis progression of less than about 0.02, 0.03, 0.04, 0.05, 0.06, 0.07, 0.08, 0.09, 0.10, 0.11, 0.12, 0.13, 0.14 or 0.15 MU/year (wherein MU/year stands for Metavir unit per year). In one embodiment, a slow fibroser has a fibrosis progression of less than about 0.060, 0.065, 0.070, 0.075, 0.080, 0.085 or 0.090 MU/year (wherein MU/year stands for Metavir unit per year). In one embodiment, a slow fibroser has a fibrosis progression of less than about 0.075 MU/year (wherein MU/year stands for Metavir unit per year).

According to the present invention, a medium fibrosis is an individual suffering from liver fibrosis with an intermediate liver fibrosis progression rate. In a medium fibroser, liver fibrosis could slowly evolve in cirrhosis, over a long period of time. In other word, a medium fibroser is at long-term risk for developing cirrhosis and any of the ensuing associated complications.

In one embodiment, a medium fibroser has an AOF progression ranging from about 0.30, 0.40, 0.50, 0.60 or 0.70%/year to about 1.00, 1.10, 1.20, 1.30, 1.40, 1.50 or 1.60%/year. In one embodiment, a medium fibroser has an AOF progression ranging from about 0.45, 0.50, 0.55, 0.60, 0.65 or 0.70%/year to about 1.25, 1.30, 1.35, 1.40 or 1.45%/year. In one embodiment, a medium fibroser has an AOF progression ranging from about 0.48, 0.50, 0.52, 0.54, 0.56, 0.58, 0.60, 0.62, 0.64, 0.66, 0.68 or 0.70%/year to about 1.30, 1.32, 1.34, 1.36, 1.38, 1.40 or 1.42%/year. In one embodiment, a medium fibroser has an AOF progression ranging from about 0.58%/year to about 1.36%/year.

In one embodiment, a medium fibroser has a fibrosis progression ranging from about 0.02, 0.03, 0.04, 0.05, 0.06, 0.07, 0.08, 0.09, 0.10, 0.11, 0.12, 0.13, 0.14 or 0.15 MU/year to about 0.060, 0.065, 0.070, 0.075, 0.080, 0.085 or 0.090 MU/year (wherein MU/year stands for Metavir unit per year). In one embodiment, a medium fibroser has a fibrosis progression ranging from about 0.070, 0.075, 0.08, 0.085, 0.09 or 0.095 MU/year to about 0.350, 0.355, 0.360, 0.365, 0.370 or 0.375 MU/year (wherein MU/year stands for Metavir unit per year). In one embodiment, a medium fibroser has a fibrosis progression ranging from about 0.075 MU/year to about 0.360 MU/year (wherein MU/year stands for Metavir unit per year).

According to the present invention, a fast fibroser is an individual suffering from liver fibrosis with a high liver fibrosis progression rate. In a fast fibroser, liver fibrosis is likely to evolve rapidly in cirrhosis. In other words, a fast fibroser is at short-term risk for developing cirrhosis and any of the ensuing associated complications.

In one embodiment, a fast fibroser has an AOF progression of more than about 1.00, 1.10, 1.20, 1.30, 1.40, 1.50 or 1.60%/year. In one embodiment, a fast fibroser has an AOF progression of more than about 1.25, 1.30, 1.35, 1.40 or 1.45%/year. In one embodiment, a fast fibroser has an AOF progression of more than about 1.30, 1.32, 1.34, 1.36, 1.38, 1.40 or 1.42%/year. In one embodiment, a fast fibroser has an AOF progression of more than about 1.36%/year.

In one embodiment, a fast fibroser has a fibrosis progression of more than about 0.30, 0.31, 0.32, 0.33, 0.34, 0.35, 0.36, 0.37, 0.38, 0.39, 0.40 MU/year (wherein MU/year stands for Metavir unit per year). In one embodiment, a fast fibroser has a fibrosis progression of more than about 0.350, 0.355, 0.360, 0.365, 0.370 or 0.375 MU/year (wherein MU/year stands for Metavir unit per year). In one embodiment, a fast fibroser has a fibrosis progression of more than about 0.360 MU/year (wherein MU/year stands for Metavir unit per year).

According to an embodiment, the individual is a slow fibroser and does not require treatment. In one embodiment, the individual is a slow fibroser and patient care consists in monitoring said individual. In one embodiment, monitoring an individual who is a slow fibroser comprises assessing the fibrosis level, as described hereinabove, at regular intervals, preferably every 2 years, 3 years, 4 years, 5 years, 6 years, 7 years, 8 years, 9 years or 10 years.

According to another embodiment, the individual is a medium fibroser and does not require immediate treatment. In one embodiment, the individual is a medium fibroser and treatment is delayed. In one embodiment, the individual is a medium fibroser and patient care consists in monitoring said individual. In one embodiment, monitoring an individual who is a medium fibroser comprises assessing the fibrosis level, as described hereinabove, at regular intervals, preferably every 6 months, every 12 months, every 18 months, every 24 months, every 30 months or every 36 months. In one embodiment, treatment is delayed until the medium fibroser is determined to suffer from clinically significant liver fibrosis, wherein clinically significant liver fibrosis corresponds to a Metavir F stage of F≥2.

According to another embodiment, the individual is a fast fibroser and requires treatment without delay. In one embodiment, the individual is a fast fibroser and patient care consists in administering without delay at least one therapeutic agent.

In one embodiment, the method of the invention is for preventing cirrhosis and complications thereof in an individual identified as a fast fibroser.

In another embodiment, the method of the invention comprises carrying out a complication screening program (preferably a program of screening of cirrhosis complications) in an individual identified as a fast fibroser, thereby administering as early as possible a prophylactic and/or curative treatment to said individual Thus, in one embodiment, the method of the invention is for treating an individual suffering from liver fibrosis and identified as a fast fibroser, said method comprising:
  identifying an individual suffering from liver fibrosis as a fast fibroser by assessing fibrosis progression in the individual as described hereinabove, and
  treating the individual suffering from liver fibrosis identified as a fast fibroser by administering without delay at least one therapeutic agent, wherein said therapeutic agent is for treating liver fibrosis, or for treating the underlying cause responsible for liver fibrosis, or both.

Examples of therapeutic agents include, but are not limited to, S-adenosyl-L-methionine, S-nitrosol-N-acetylcystein, silymarin, phosphatidylcholine, N-acetylcysteine, resveratrol, vitamin E, pentoxyphilline (or pentoxyfilline) alone or in combination with tocopherol, pioglitazone alone or in combination with vitamin E, lovaza (fish oil), PPC alone or in combination with an antiviral therapy (e.g. IFN), INT747, peginterferon 2b (pegylated IFNalpha-2b), a combination of infliximab, and ribavirin, stem cell transplantation (in particular MSC transplantation), candesartan, losartan, telmisartan, irbesartan, ambrisentan, FG-3019, *Phyllanthus uriaria*, Fuzheng Huayu, warfarin, insulin, colchicine, corticosteroids, naltrexone, RF260330, sorafenib, gleevec, nilotinib, pirfenidone, halofuginone, polaorezin, gliotoxin, sulfasalazine, rimonabant, simtuzumab, GR-MD-02, boceprevir, telaprevir, simeprevir, sofosbuvir, daclatasvir, elbasvir, grazoprevir, velpatasvir, lamivudine, adefovir dipivoxil, entecavir, telbivudine, tenofovir, clevudine, ANA380, zadaxin, CMX 157, ARB-1467, ARB-1740, ALN-HBV, BB-HB-331, Lunar-HBV, ARO-HBV, Myrcludex B, GLS4, NVR 3-778, AIC 649, JNJ56136379, ABI-H0731, AB-423, REP 2139, REP 2165, GSK3228836, GSK33389404, RNaseH Inhibitor, GS 4774, INO-1800, HB-110, TG1050, HepTcell, TomegaVax HBV, RG7795, SB9200, EYP001, CPI 431-32, topiramate, disulfiram, naltrexone, acamprosate, baclofen, methadone, buprenorphine, orlistat, metformin, atorvastatin, ezetimine, ARBs, EPL, EPA-E, multistrain biotic (*L. rhamnosus, L. bulgaricus*), obeticholic acid, elafibranor (GFT505), DUR-928, GR-MD, 02, aramchol, RG-125, cenicriviroc CVC, rosiglitazone, MSDC-0602K, GS-9674, LJN452, LMB763, EDP-305, elafibranor, saroglitazar, IVA337, NGM282, PF-05231023, BMS-986036, aramchol, volixibat, GS-0976, liraglutide, semaglutide exenatide, taspoglutide, taurine, polyenephosphatidylcholine, MGL-3196, vitamin C, GS-4997, sitagliptin, alogliptin, vildagliptin, saxagliptin, linagliptin, PXS-4728A, VLX-103, hyperimmune bovine clostrum, nalmefene, emricasan, milk thistle; and probiotics and combinations thereof.

In one embodiment, the at least one therapeutic agent is for treating liver fibrosis and/or ameliorating or alleviating the symptoms associated with liver fibrosis. In one embodiment, the at least one therapeutic agent is for treating liver fibrosis and is selected from the group consisting of simtuzumab, GR-MD-02, stem cell transplantation (in particular MSC transplantation), *Phyllanthus urinaria*, Fuzheng Huayu, S-adenosyl-L-methionine, S-nitrosol-N-acetylcystein, silymarin, phosphatidylcholine, N-acetylcysteine, resveratrol, vitamin E, losartan, telmisartan, naltrexone, RF260330, sorafenib, gleevec, nilotinib, INT747, FG-3019, oltipraz, pirfenidone, halofuginone, polaorezin, gliotoxin, sulfasalazine, rimonabant and combinations thereof.

In another embodiment, the at least one therapeutic agent is for treating the underlying cause responsible for liver fibrosis, and/or ameliorating or alleviating the symptoms associated with the underlying cause responsible for liver fibrosis.

In one embodiment, the underlying cause responsible for liver fibrosis is selected from the group consisting of a hepatitis viral infection, a hepatotoxicity, a non-alcoholic fatty liver disease (NAFLD), an autoimmune disease, a metabolic liver disease and a disease with secondary involvement of the liver.

Hepatitis viral infection may be caused by a virus selected from the group consisting of hepatitis C virus, hepatitis B virus and hepatitis D virus. Hepatotoxicity may be alcohol induced hepatotoxicity and/or drug-induced hepatotoxicity. Non-alcoholic fatty liver diseases (NAFLD) encompass nonalcoholic steatohepatitis (NASH), including both active NASH, inactive NASH and fibrotic NASH.

In one embodiment, the underlying cause responsible for liver fibrosis is a viral infection and the at least one therapeutic agent is selected from the group consisting of interferon, peginterferon 2b (pegylated IFNalpha-2b), infliximab, ribavirin, boceprevir, telaprevir, simeprevir, sofosbuvir, daclatasvir, elbasvir, grazoprevir, velpatasvir, lamivudine, adefovir dipivoxil, entecavir, telbivudine, tenofovir, clevudine, ANA380, zadaxin, CMX 157, ARB-1467, ARB-1740, ALN-HBV, BB-HB-331, Lunar-HBV, ARO-HBV, Myrcludex B, GLS4, NVR 3-778, AIC 649, JNJ56136379, ABI-H0731, AB-423, REP 2139, REP 2165, GSK3228836, GSK33389404, RNaseH Inhibitor, GS 4774, INO-1800, HB-110, TG1050, HepTcell, TomegaVax HBV, RG7795, SB9200, EYP001, CPI 431-32 and combinations thereof.

In one embodiment, the underlying cause responsible for liver fibrosis is a hepatitis B and the at least one therapeutic agent is selected from the group consisting of interferon, peginterferon 2b (pegylated IFNalpha-2b), infliximab, ribavirin, lamivudine, adefovir dipivoxil, entecavir, telbivudine, tenofovir, clevudine, ANA380, zadaxin, CMX 157, ARB-1467, ARB-1740, ALN-HBV, BB-HB-331, Lunar-HBV, ARO-HBV, Myrcludex B, GLS4, NVR 3-778, AIC 649, JNJ56136379, ABI-H0731, AB-423, REP 2139, REP 2165, GSK3228836, GSK33389404, RNaseH Inhibitor, GS 4774, INO-1800, HB-110, TG1050, HepTcell, TomegaVax HBV, RG7795, SB9200, EYP001, CPI 431-32 and combinations thereof.

In one embodiment, the underlying cause responsible for liver fibrosis is a hepatitis C and the at least one therapeutic agent is selected from the group consisting of interferon, peginterferon 2b (pegylated IFNalpha-2b), infliximab, ribavirin, boceprevir, telaprevir, simeprevir, sofosbuvir, daclatasvir, elbasvir, grazoprevir, velpatasvir and combinations thereof.

In one embodiment, the underlying cause responsible for liver fibrosis is excessive alcohol consumption and the at least one therapeutic agent is selected from the group consisting of topiramate, disulfiram, naltrexone, acamprosate and baclofen.

In one embodiment, the underlying cause responsible for liver fibrosis is excessive drug consumption and the at least one therapeutic agent is selected from the group consisting of methadone, buprenorphine, and naltrexone.

In one embodiment, the underlying cause responsible for liver fibrosis is a non-alcoholic fatty liver disease (NAFLD) and the at least one therapeutic agent is selected from the group consisting of orlistat, metformin, pioglitazone, atorvastatin, ezetimine, vitamin E, sylimarine, pentoxyfylline, ARBs, EPL, EPA-E, multistrain biotic (*L. rhamnosus, L. bulgaricus*), simtuzumab, obeticholic acid, elafibranor (GFT505), DUR-928, GR-MD, 02, aramchol, RG-125, cenicriviroc CVC and combinations thereof.

In one embodiment, the underlying cause responsible for liver fibrosis is a nonalcoholic steatohepatitis (NASH), preferably fibrotic NASH, and the at least one therapeutic agent is selected from the group consisting of insulin sensitizers (such as rosiglitazone, pioglitazone and MSDC-0602K); farnesoid X receptor (FXR) agonists (such as obeticholic acid (also referred to as OCA), GS-9674, LJN452, LMB763 and EDP-305); Peroxisome Proliferator-Activated Receptor α/δ (PPAR α/δ) agonists (such as elafibranor, saroglitazar and IVA337); fibroblast growth factor 19 (FGF19) analogs (such as NGM282); fibroblast growth factor 21 (FGF21) analogs (such as PF-05231023); recombinant FGF21 (such as BMS-986036); stearoyl-coenzyme A desaturase 1 (SCD1) inhibitors (such as aramchol); apical sodium-dependent bile acid transporter (ASBT) inhibitors (such as volixibat); acetyl-coA carboxylase (ACC) inhibitors (such as GS-0976); glucagon-like peptide-1 (GLP-1) analogs (such as liraglutide, semaglutide exenatide and taspoglutide); ursodeoxycholic acid and norursodeoxycholic acid (NorUDCA); taurine; polyenephosphatidylcholine; thyroid hormone receptor (THR) β-agonists (such as MGL-3196); antioxidant agents (such as vitamin E and vitamin C); apoptosis signal-regulating kinase 1 (ASK1) inhibitors (such as GS-4997); DPP-4 inhibitors (such as sitagliptin, alogliptin, vildagliptin, saxagliptin, and linagliptin); vascular adhesion protein-1 (VAP-1) inhibitors (such as PXS-4728A);

phosphodiesterase-4 (PDE-4) inhibitors; angiotensin II-1 type receptor antagonists (such as losartan and telmisartan); anti-inflammatory compounds (such as cenicriviroc, VLX-103 (oral pentamidine) and hyperimmune bovine clostrum); Toll-like receptor 4 antagonists (such as nalmefene); caspase inhibitors (such as emricasan); pentoxifylline; S-adenosyl-methionine; milk thistle; and probiotics.

Other objects, advantages and features of the present invention will become more apparent upon reading of the following non-restrictive description of preferred embodiments thereof, given by way of examples with reference to the accompanying figures.

BRIEF DESCRIPTION OF THE DRAWINGS

FIGS. 1-7 are to be read with regard to Example 1.

FIG. 1 is a graph showing the correlation of progression rates between Metavir F and area of fibrosis ($r_s=0.77$, $r_p=0.90$, $p<10^{-4}$) as a function of Metavir fibrosis (F) stage. $r_s$ is the coefficient of correlation of Spearman; $r_p$ is the coefficient of correlation of Pearson.

FIG. 2 is a graph showing the progression rate of fibrosis as a function of Metavir F stage. The progression rate of Metavir F (F) or area of fibrosis (AOF) is correlated to Metavir F stages ($r_s=0.58$, $p<10^{-4}$, $r_s=0.49$, $p<10^{-4}$, respectively) and significantly different as a function of Metavir F grade (ANOVA: $p<10^{-4}$, $p=0.001$, respectively).

FIG. 4 is a graph showing the AOF as a function of cause duration according to CLD cause (alcoholic in black and viral in grey) and to Metavir F stage.

FIG. 5 is the AOF progression rate as a function of cause duration according to Metavir fibrosis (F) stage.

The curve has an inverse shape (1/x) by definition.

Figure 6A:
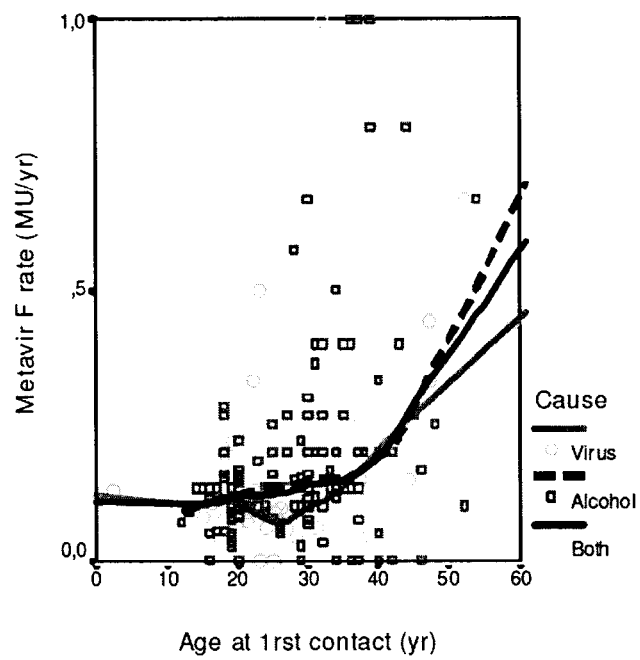
Figure 6B:
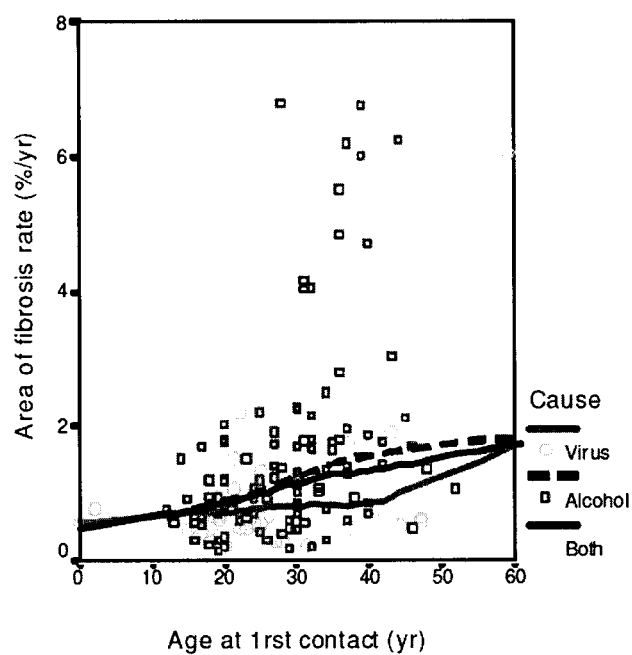

FIGS. 6A and 6B are the relationship between fibrosis progression rate, Metavir fibrosis stage (6A) and AOF (6B) and age at 1st contact. Lines are provided by polynomial regression. The axis of AOF progression was truncated at 3.

Figure 7:
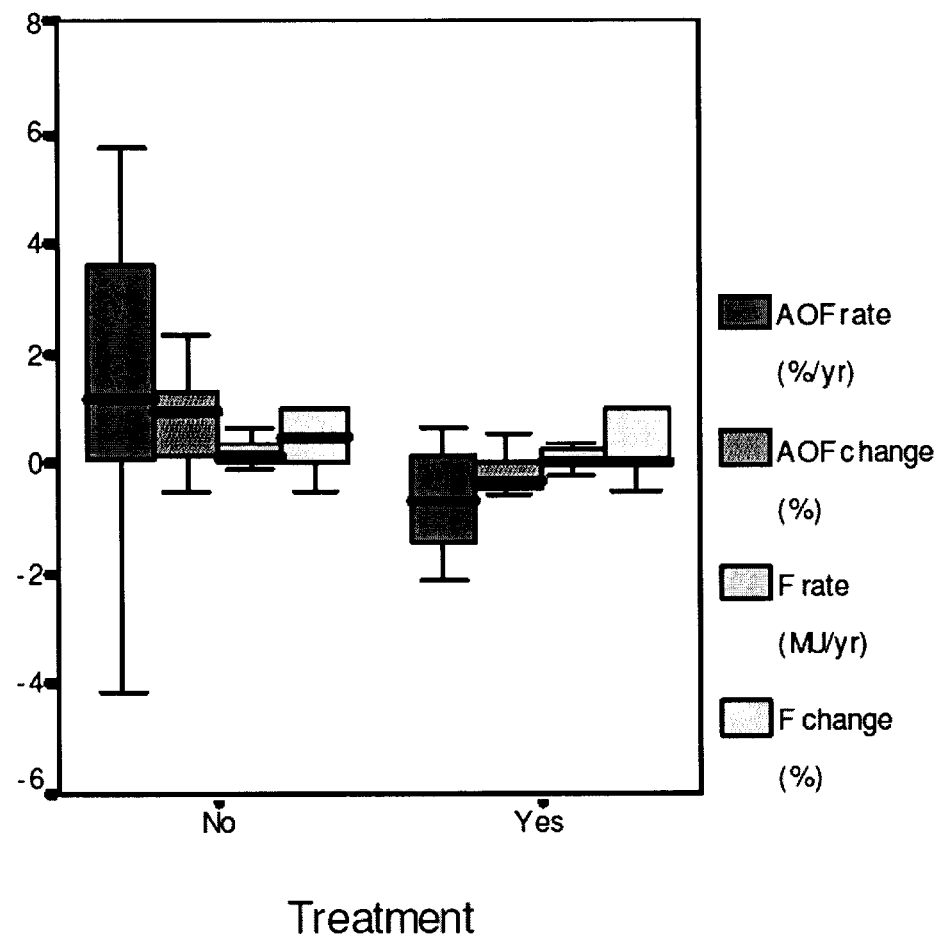

FIG. 7 is the effects of antifibrotic treatment on area of fibrosis and Metavir F stage. Box plots indicate median, quartiles and extremes.

FIGS. 8A-16 are to be read with regard to Example 2.

Figures 8A, 8B:
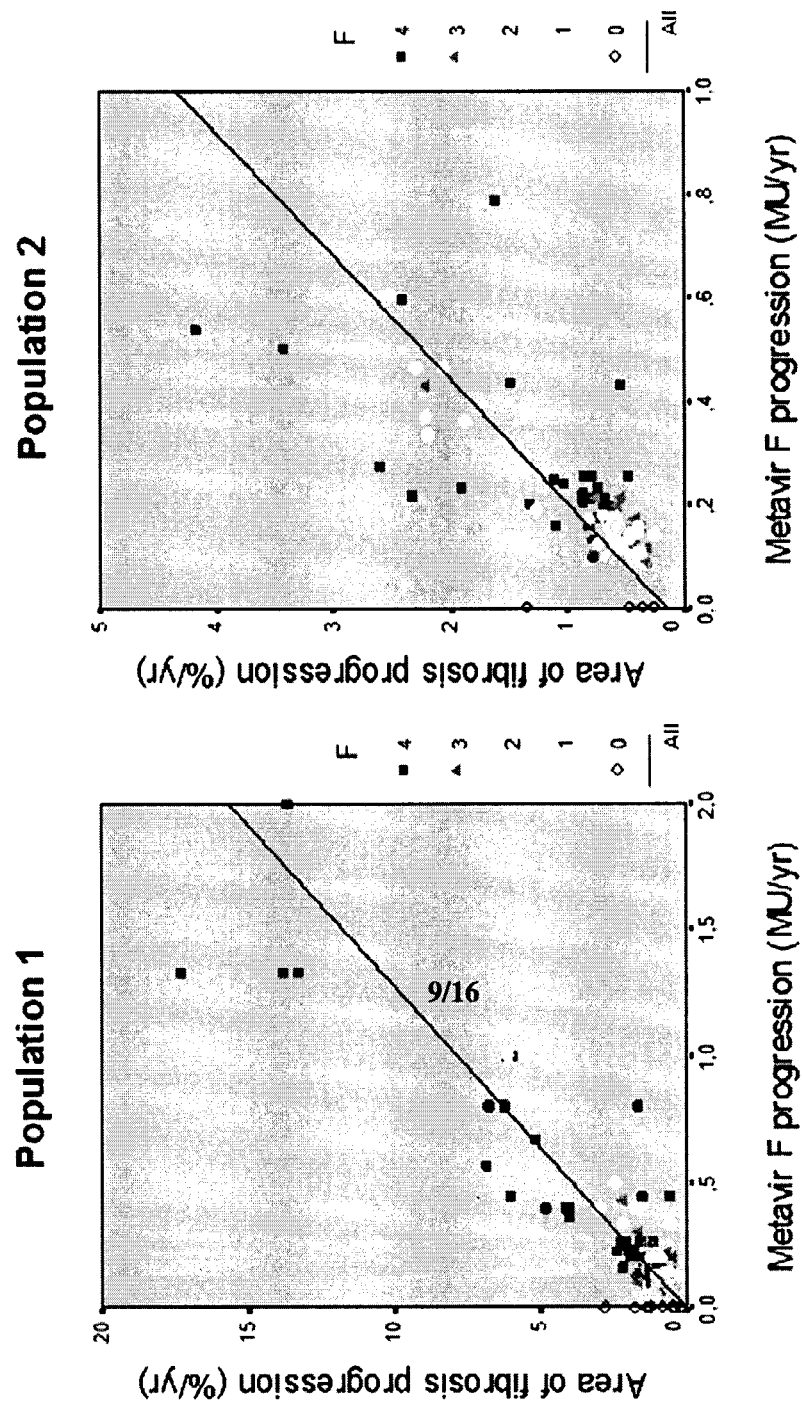

FIGS. 8A and 8B are a combination of graphs showing the correlation between Metavir fibrosis (F) stage and area of fibrosis (AOF) progression in populations 1 (8A) and 2 (8B) of Example 2. Lines depict linear regression.

FIGS. 9A-9D are a combination of graphs showing relationship between Metavir fibrosis (F) stage (9A and 9C) or area of fibrosis (AOF) (9B and 9D) progression, during cause duration, as a function of Metavir fibrosis (F) stage at inclusion age in populations 1 (9A and 9B) and 2 (9C and 9D).

FIGS. 10A-10D are a combination of graphs showing the correlation between Metavir fibrosis (F) stage (10A and 10C) or area of fibrosis (AOF) (10B and 10D) progression and respective predicted progression in populations 1 (10A and 10B, alcoholic CLD only) and 2 (10C and 10D, viral CLD).

FIGS. 11A-11D show the relationship between Metavir fibrosis (F) stage (11A and 11C) or area of fibrosis (AOF) (11B and 11D) and cause duration in populations 1 (11A and 11B) and 2 (11C and 11D). Curves depict Lowess regression.

FIGS. 12A-12D show the relationship between Metavir fibrosis (F) stage (12A and 12C) or area of fibrosis (AOF) (12B and 12D) progression and start age in populations 1 (12A and 12B) and 2 (12C and 12D). Curves depict Lowess regression.

FIGS. 13A-13D show the relationship between Metavir fibrosis (F) stage (13A and 13C) or area of fibrosis (AOF) (13B and 13D) and start age in populations 1 (13A and 13B) and 2 (13C and 13D). Curves depict Lowess regression.

FIGS. 14A-14E show the relationship between Metavir fibrosis (F) stage progression (14A and 14D) or area of fibrosis progression (14B and 14E) or area of fibrosis (14C and 14F) and inclusion age in populations 1 (14A, 14B and 14C) and 2 (14D, 14E and 14F). Curves depict Lowess regression:

FIGS. 15A-15D show the relationship between fibrosis characteristics, i.e., Metavir fibrosis (F) stage (15A), area of fibrosis (15B and 15D), and Metavir fibrosis (F) stage progression (15C), and cause duration (15A, 15B and 15D) or area of fibrosis progression (15C) showing different fibrosers as a function of fibrosis progression in population 2. Curves depict Lowess regression.

Figure 16:
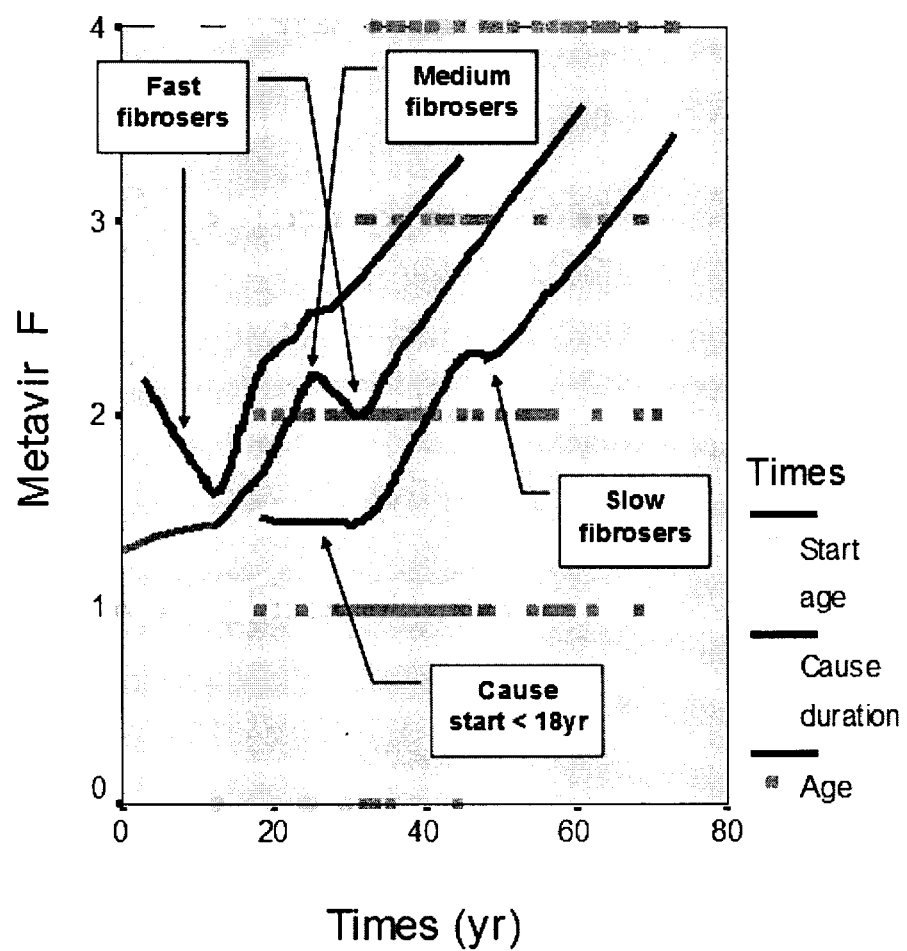

FIG. 16 shows the impact of special patient subgroups on curves of Metavir fibrosis (F) stage as a function of different times in population 2. The impact was determined according to the method shown in FIG. 11A.

Figure 17:
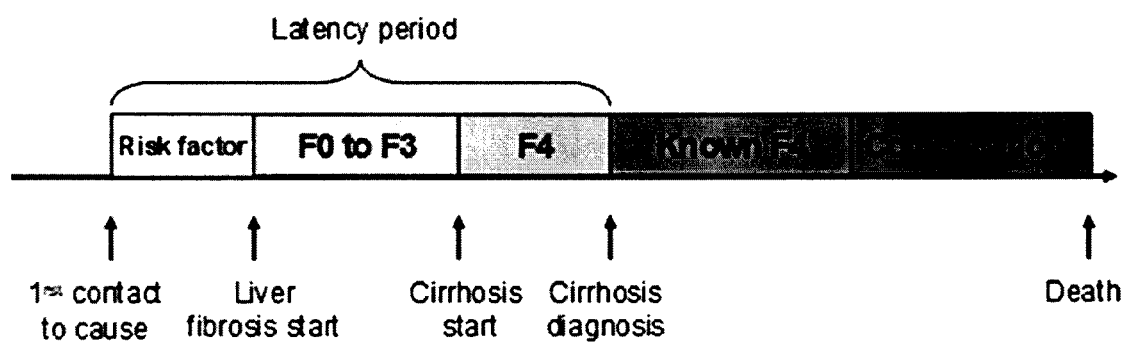

FIG. 17 is a diagram depicting the evolution of liver fibrosis over time and the corresponding liver fibrosis Metavir classification into five stages from F0 to F4. According to the Metavir classification, an F2 stage means that fibrosis is clinically significant, whereas a F4 stage corresponds to the ultimate stage, namely cirrhosis.

EXAMPLES

Example 1

Methods
1. Patients
Populations

All 201 patients included in this study were admitted to the hepatogastroenterology unit of the University hospital in Angers, France. A $1^{st}$ population of 185 patients (all of which had been subjected to one liver biopsy) was selected according to the availability of an estimation of the contact date (or exposure) to the risk factor (or cause) of CLD. The difference between inclusion date and contact date is herein called "duration of cause". A $2^{nd}$ population of 16 patients (all of which had been subjected to two liver biopsies) was selected.

Population 1

The 185 patients included in this population were admitted for alcoholic liver disease, or for chronic viral hepatitis B or C. Patients were included who had drunk at least 50 g of alcohol per day for the past five years or were positive for serum hepatitis B surface antigen or C antibodies. None of the patient had clinical, biological, echographic or histological evidence of other causes of chronic liver disease (Wilson's disease, hemochromatosis, a1-antitrypsin deficiency, biliary disease, auto-immune hepatitis, hepatocellular carcinoma). Blood samples were taken at entry and a transcostal (suction needle) or transjugular (cutting needle) liver biopsy was performed within one week.

These patients might have had liver decompensation and different CLD causes. In fact, the duration of cause was recorded in only 179 patients but in the 6 other patients with Metavir F stage 0, the rate of Metavir F progression could be fixed at 0 by definition. However, the area of fibrosis could be measured in only 153 patients due to specimen fragmentation in 26 patients whereas the progression rate could not be fixed in the 6 patients with Metavir F stage 0 since baseline area of fibrosis is not null. The date of $1^{st}$ exposure was estimated according to the recording of 1st blood transfusion or drug abuse in viral CLD and the $1^{st}$ date of chronic excessive alcohol intake in alcoholic CLD. This population allowed calculating an estimated progression rate of fibrosis. In addition, explanatory variables of progression were recorded a posteriori.

Population 2

These 16 patients had two liver biopsies, different CLD causes and 10 underwent putative antifibrotic treatment like interferon and sartan between both biopsies. This population allowed measuring an observed progression rate of fibrosis. In addition, explanatory variables of progression were recorded a priori, thus being true predictive factors.

2. Clinical Evaluation

A full clinical examination was performed by a senior physician. The recorded variables were: age, age at $1^{st}$ contact to the cause of liver disease (available only for alcoholic patients and in C hepatitis attributed to blood transfusion and drug abuse), sex, size, body weight (before an eventual paracentesis), mean alcohol consumption (g/d) before eventual withdrawal, duration of alcohol abuse, alcohol withdrawal, duration of alcohol withdrawal, known duration of liver disease (since the first clinical or biochemical abnormality suggestive of CLD), Child-Pugh score and other clinical abnormalities. Population 1 underwent also an upper gastro-intestinal endoscopy to evaluate signs of portal hypertension and liver Doppler-ultrasonography.

3. Blood Tests

Analyses of blood samples provided the following measurements: hemoglobin, mean corpuscular volume, lymphocyte count, platelet count, cholesterol, urea, creatinine, sodium (NA), bilirubin, γ-glutamyl transpeptidase (GGT), alkaline phosphatases (ALP), aspartate aminotransferase (AST) and alanine aminotransferase (ALT), albumin (ALB), α1 and α2-globulins, β-globulins, γ-globulins, βγ-block, prothrombin index (PI), apolipoprotein A1 (ApoA1). Some of them are indirect blood markers of fibrosis (1).

The direct blood markers of fibrosis used in this study were the following: α-2 macroglobulin (α2M), the N-terminal peptide of type III procollagen (P3P), hyaluronic acid (HA), TGF β1, and laminin. The following blood tests were calculated: AST/ALT ratio, PGA score (2), PGAA score (3), APRI (4), different FibroMeters (5), and Hepascore (6). Sera were kept at −80° C. for a maximum of 48 months for assay.

4. Liver Histological Assessment

Microscopic Analysis

Biopsy specimens were fixed in a formalin-alcohol-acetic solution and embedded in paraffin; 5 µm thick sections were stained with haematoxylin-eosin-saffron and 0.1% picro-sirius red solution. Fibrosis was staged by two independent pathologists according to the Metavir staging (7). The Metavir staging is also well adapted to the semi-quantitative evaluation of fibrosis in alcoholic CLD since porto-septal fibrosis is more frequent and developed than centrolobular fibrosis (8). Observers were blinded for patient characteristics. When the pathologists did not agree, the specimens were re-examined under a double-headed microscope to analyse discrepancies and reach a consensus. All specimens were also evaluated according to the following grades: Metavir activity (7), steatosis and centrolobular fibrosis (CLF) as previously described (9).

Image Analysis

AOF was measured on the same sections as the microscopic analysis using a Leica Quantimet Q570 image processor as previously described (9). Fractal dimension of fibrosis was also measured in population 2 (10).

5. Observers

Overall there were 2 pathologists with 1 senior expert and 1 junior expert working in academic hospital. Image analysis was performed by the junior expert pathologist experienced in this technique.

6. Statistical Analysis

Quantitative variables were expressed as mean±SD, unless otherwise specified. The Pearson's rank correlation coefficient ($r_p$) was used for correlations between continuous variables or Spearman correlation coefficient ($r_s$) when necessary. To assess independent predictors, multiple linear regression for quantitative dependent variables and binary logistic regression for qualitative dependent variables were used with forward stepwise addition of variables. The predictive performance of each model is expressed by the adjusted $R^2$ coefficient ($_aR^2$) and by the diagnostic accuracy, i.e. true positives and negatives, respectively. A α risk<5% for a two-sided test was considered statistically significant. The statistical software used was SPSS version 11.5.1 (SPSS Inc., Chicago, Ill., USA).

7. Example of Mathematical Function

The estimation of the progression rate (PR) is provided by multiple linear regression according to the following formula: $PR = a_0 + a_1 x_1 + a_2 x_2 + \ldots$, where $a_x$ is the coefficient of marker or variable $x_x$ and $a_0$ is a constant.

An example of formula for the PR of area of fibrosis is the predictive model including AST/ALT, cause duration, firm liver, β-globulins, and FibroMeter™ where the coefficients are the followings:

Constant: −0.0978158087539 with limits of confidence interval at 95%: 0.8363614252041 & −1.035103236918, AST/ALT: 0.5412244415007 with limits of confidence interval at 95%: 2.07804027617.e−006 & 0.3283727153579, Cause duration: −0.07623687627859 with limits of confidence interval at 95%: 5.016575306101.e−011 & −0.09671608407235, Firm liver: 0.7172332316927 with limits of confidence interval at 95%: 0.006563850544752 & 0.2047931685256, β-globulins: 0.1594071294621 with limits of confidence interval at 95%: 0.001915414369681 & 0.06022006972876, FibroMeter™: 1.15299980586 with limits of confidence interval at 95%: 0.002487655344947 & 0.4161078148282.

Results

1. General Characteristics

The general characteristics of different populations are presented in table 1.

TABLE 1

Main characteristics of populations

| | Population | |
|---|---|---|
| | 1 | 2 |
| N | 185 | 16 |
| Age (y) | 48.5 ± 12.3 | 44.5 ± 10.4 |
| Sex (% M) | 67.6 | 62.5 |
| Cause (% virus) | 26.5 | 75.0 |

TABLE 1-continued

Main characteristics of populations

| | Population | |
|---|---|---|
| | 1 | 2 |
| Metavir F (%): | | |
| 0 | 9.7 | 18.8 |
| 1 | 18.9 | 31.3 |
| 2 | 15.1 | 25.0 |
| 3 | 8.1 | 6.2 |
| 4 | 48.1 | 18.8 |
| Complication (%) | 21.6 | 12.5 |

2. Main Characteristics of Fibrosis Progression

There were calculated in population 1. The rate of progression, expressed in Metavir unit (MU) per year, ranged from 0 to 2.0 MU/yr for Metavir F (mean: 0.22±0.29, median: 0.13) and from 0.1 to 17.2%/yr for the area of fibrosis (mean: 1.8±2.6, median: 1.0).

Figure 1:
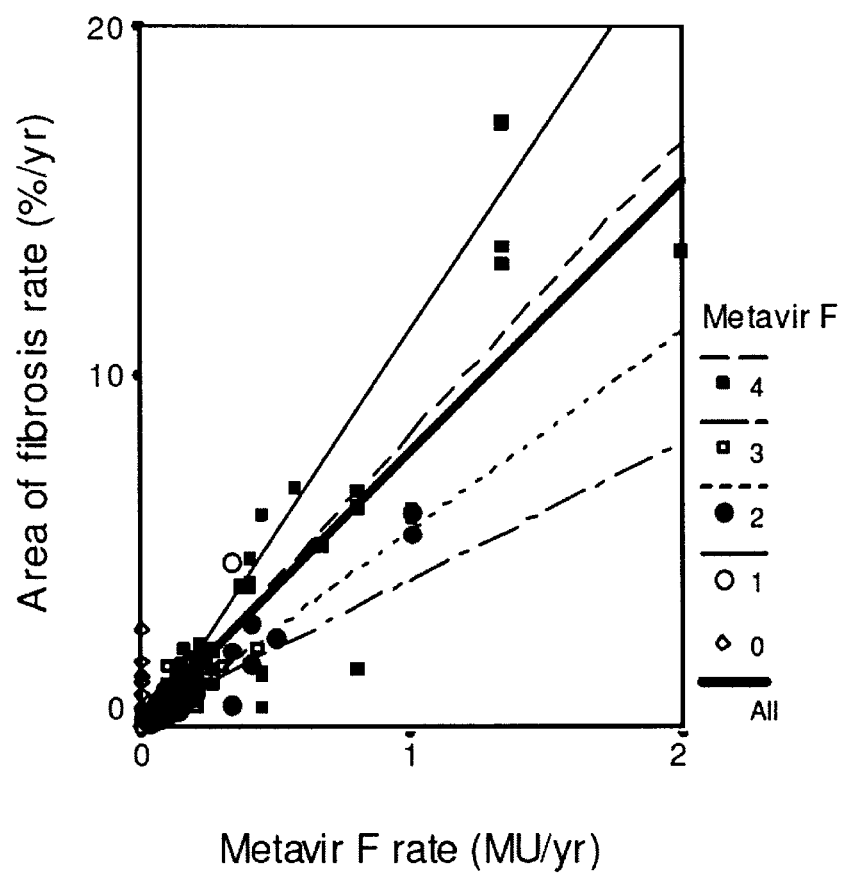
Figure 2:
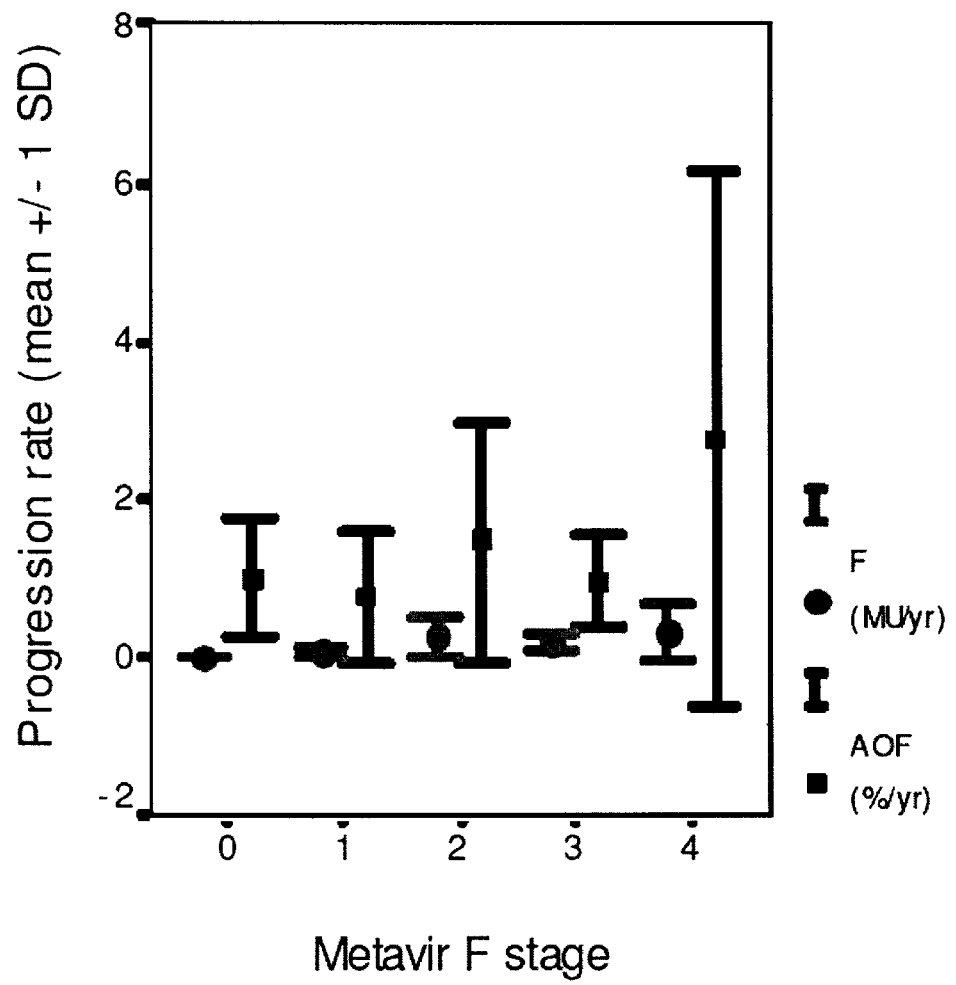

Both fibrosis progression rates were highly correlated (FIG. 1). The progression rate of fibrosis increased as a function of fibrosis F stage (FIG. 2). We then tested the other factors linked to the progression of fibrosis.

3. Predictive Factors of Fibrosis Progression

Metavir F Progression

The most marked correlations of Metavir F progression were observed with Metavir F stage ($r=0.33$, $p<10^{-4}$), the area of fibrosis ($r=0.28$, $p<10^{-4}$), age at $1^{st}$ contact ($r=0.46$), cause duration ($r=-0.48$, $p<10^{-4}$), P3P ($r=0.26$, $p<10^{-4}$), HA ($r=0.27$, $p<10^{-4}$), PI ($r=-0.22$, $p<10^{-4}$), GGT ($r=0.32$, $p<10^{-4}$), AST/ALT ($r=0.38$, $p<10^{-4}$), FibroMeter™ ($r=0.27$, $p<10^{-4}$), PGA score ($r=0.27$, $p<10^{-4}$) and PGAA score ($r=0.28$, $p<10^{-4}$). The only significant links with qualitative variables were observed with fry-block ($p=0.03$) and sex ($p=0.001$).

With linear regression, the independent predictors of the Metavir F progression were: AST/ALT, cause duration, Metavir F stage and PI ($_aR^2=0.605$). CLD cause had no independent role ($p=0.63$). If Metavir F stage was removed, there was no pathological variable in the predictive model: cause duration, AST/ALT, age at $1^{st}$ contact, and FibroMeter™ ($_aR^2=0.488$). It should be noted that "age at $1^{st}$ contact"+"cause duration"=age, however if the two former were removed, the latter was not selected, while $_aR^2$ decreased to 0.195 with AST/ALT and sex.

Area of Fibrosis Progression

The most marked correlations of the area of fibrosis progression were observed with Metavir F stage ($r=0.32$, $p<10^{-4}$), the area of fibrosis ($r=0.41$, $p<10^{-4}$), age at $1^{st}$ contact ($r=0.43$), cause duration ($r=-0.43$, $p<10^{-4}$), HA ($r=0.34$, $p<10^{-4}$), PI ($r=-0.24$, $p<10^{-4}$), β-globulins ($r=0.32$, $p<10^{-4}$), AST/ALT ($r=0.51$, $p<10^{-4}$), FibroMeter™ ($r=0.29$, $p<10^{-4}$), PGA score ($r=0.29$, $p<10^{-4}$) and PGAA score ($r=0.30$, $p<10^{-4}$). Several significant links with qualitative variables were observed: βγ-block ($p=0.004$), sex ($p=0.004$), firm liver ($p=0.04$), splenomegaly ($p=0.02$), ascites ($p=0.001$), EV grade ($p=0.04$), collateral circulation ($p=0.001$) and the cause of CLD ($p=0.03$).

With linear regression, the independent predictors of the area of fibrosis progression were: AST/ALT, cause duration, area of fibrosis, and β-globulins ($_aR^2=0.716$). It should be noted that steatosis had a borderline signification ($p=0.057$) but not activity ($p=0.53$) and CLD cause ($p=0.39$). If the area of fibrosis was removed, the Metavir F stage took its place in the model ($_aR^2=0.689$) and if Metavir F stage was removed, i.e. without any pathological variables, the predictive model included AST/ALT, cause duration, firm liver, β-globulins, and PI ($_aR^2=0.643$). If "cause duration" was removed, "age at $1^{st}$ contact" took its place in the model ($_aR^2=0.643$) and if "age at $1^{st}$ contact" stage was removed, the model included objective variables: AST/ALT, age, β-globulins and A2M with $_aR^2=0.509$.

4. Kinetics of Fibrosis Progression

Estimated Progression (Population 1)

Figure 3A:
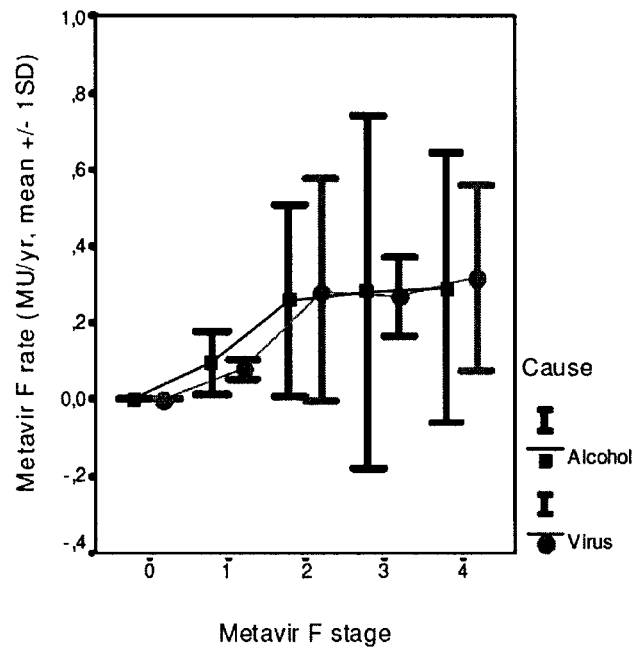
FIGS. 3A and 3B are a combination of graphs showing the fibrosis progression rates for Metavir F (3A) and AOF (3B) in alcoholic and viral chronic liver disease (CLD). Transition lines are drawn only to show the differences between patient groups.
Figure 3B:
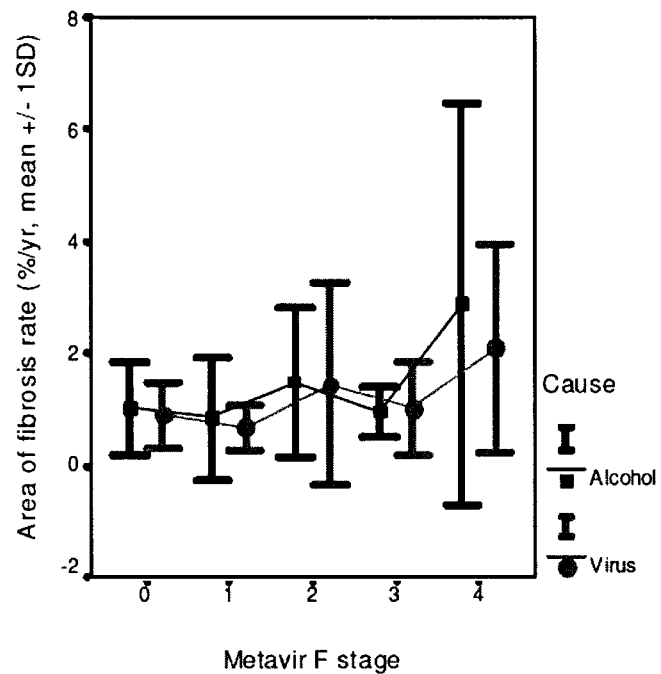

FIG. 3 shows a progressive but irregular increase in fibrosis rate as a function of Metavir F stage. As expected, the progression rate of Metavir F stage was more linked to F stage than did the area of fibrosis as also reflected by correlation coefficients ($r_s=0.58$ and 0.49, respectively, $p<10^{-4}$). FIG. 3 shows a rather stable progression rate of area of fibrosis from F stage 0 to 3 and a dramatic increase in patients with cirrhosis whereas the increase was progressive through all F stages for progression rate of Metavir F stage.

Figure 4:
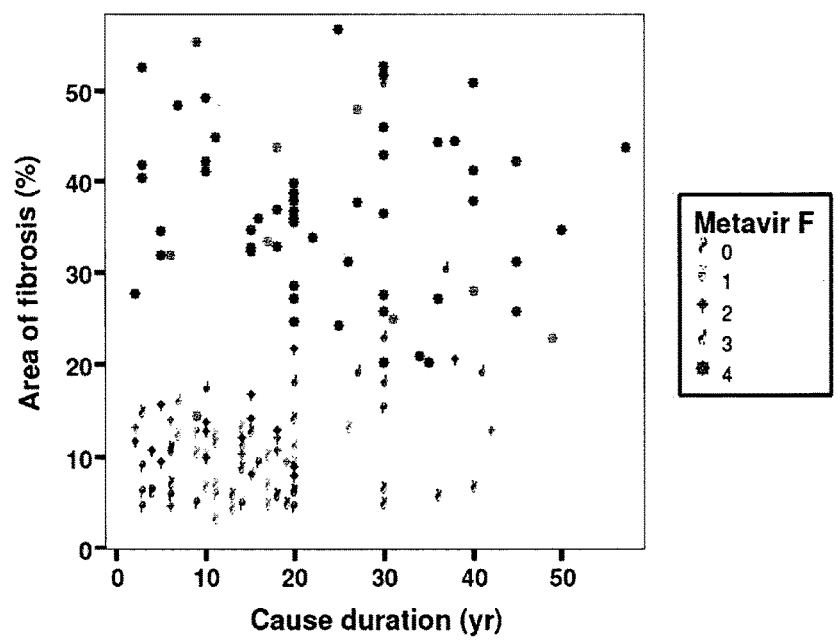

The correlation between the area of fibrosis and cause duration was weak ($r_p=0.32$, $p<10^{-4}$). In fact, FIG. 4 shows that the area of fibrosis as a function of cause duration markedly varied among patients, so patients might develop cirrhosis within a short period and others after a prolonged period. However, all patients with the fastest rate, as expected, and those with the longest follow-up, as less expected, had cirrhosis. A short cause duration was surprising in cirrhosis, however this was mainly observed in alcoholic CLD. Moreover, patient age was significantly lower when cause duration was <15 yr: 45.5±8.9 vs 55.0±10.2 yr for 15 yr ($p=0.002$) in alcoholic CLD whereas the figures were similar in viral CLD: 54.4±14.4 vs 56.6±15.2 yr ($p=0.81$), respectively. This figure also does not suggest particular groups of patients according to progression rate.

Figure 5:
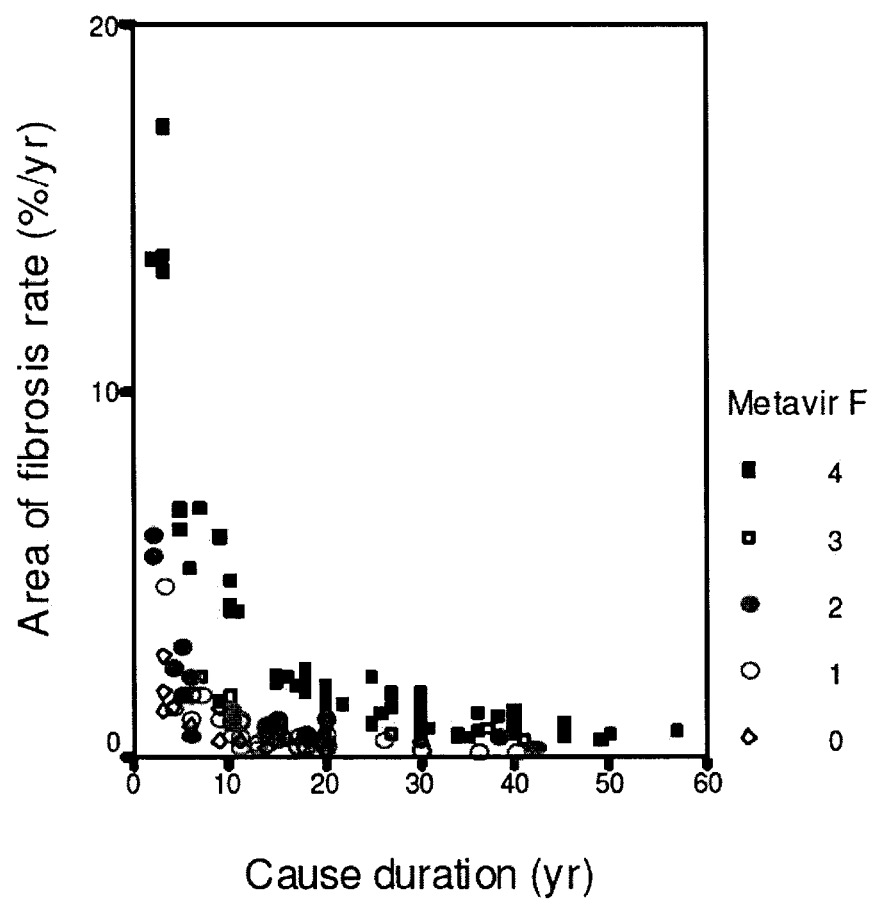

The graph of AOF progression plotted against cause duration (FIG. 5) clearly shows that individual patients had different patterns of progression rate of area of fibrosis within each F stage. In fact, previous multivariate analyses indicated that "cause duration" or "age at $1^{st}$ contact" was the main clinical independent predictor of Metavir F or area of fibrosis progression. FIG. 6 shows that the F progression dramatically increased by 40 years in viral and alcoholic CLD. However, the AOF progression displayed a linear increase over age in alcoholic CLD whereas there was a plateau followed by a linear increase by 40 years in viral CLD.

Observed Progression (Population 2)

The mean interval between biopsies (follow-up duration) was 4.1±2.6 years in the whole group and 4.8±2.5 in the 6 patients without treatment compared to 3.6±2.6 ($p=0.38$) in the 10 patients with anti-fibrotic treatment between the 2 liver biopsies. The yearly rate of progression in untreated patients was for Metavir F: mean: 0.17±0.27, median: 0.09 MU and for the area of fibrosis: mean: 1.3±3.4, median: 1.2%. These values were not significantly different than those estimated ($p=0.66$ for F and $p=0.72$ for AOF).

AOF was far more sensitive than Metavir F stage to detect effects of anti-fibrotic treatment: percent changes in AOF: $p=0.03$, progression rate of AOF: $p=0.09$; percent changes in F stage: $p=0.85$, progression rate of F stage: $p=0.71$ (by Mann-Whitney test, FIGS. 10A-10D) or proportion of F stage increase: $p=0.61$ (by McNemar $\chi^2$ test).

Example 2

Fibrosis progression was calculated as the ratio fibrosis level/cause duration, with fibrosis level indicating stage or amount AOF. So, this is a mean value as a function of time. As the main aim was to precisely describe fibrosis progression, through the amount of fibrosis reflected by the AOF, we used LB as reference for fibrosis level determination and we chose for the non invasive diagnosis a blood test that can both evaluate fibrosis staging and AOF (14). For time recording, we used two descriptors of fibrosis progression: the progression rate and the progression course. The progression rate is a mean as a function of cause duration, cause duration being the time between the age when the cause started ("start age") and the age at inclusion when fibrosis level was measured ("inclusion age"). Progression course is the trend as a function of time (increase, stability, decrease). Thus, according to the methods used for fibrosis determination (LB or non-invasive test) and duration recording (retrospective/transversal or prospective/longitudinal), we distinguished 4 methods to calculate fibrosis progression. Their characteristics, advantages and limits are detailed in table 2. Because the availability of these methods has markedly evolved as a function of time, we had to indirectly compare them by collecting different populations in our database.

Patients
Population Aims (Table 3)

5 populations including 1456 patients were used. All patients included in this study were admitted to the Hepato-gastroenterology unit of the University hospital in Angers, France, except in population 3 that is described elsewhere (15).

Populations 1 and 2 were selected according to the availability of estimation of the age when the cause started ("start age"). The period between start age and age at inclusion when fibrosis level was measured ("inclusion age"), was called "cause duration". Population 1 provided comparison between alcoholic and viral CLD. Population 2 with viral CLD had a sufficient high number of patients to validate the previous viral subpopulation and to allow subgroup analysis. Population 3 was a large population with viral CLD providing a validation of inclusion age effect. Population 4 allowed validating in patients with 2 LB the previous progression estimated with 1 LB. Finally, population 5 was used to validate the progression calculated with two blood tests.

Population Characteristics (Table 4)
Population 1—

It included 185 patients with alcoholic CLD or chronic hepatitis B or C between 1994 and 1996. This population is detailed elsewhere (16). The date of $1^{st}$ cause exposure was estimated according to the $1^{st}$ date of chronic excessive alcohol intake for alcoholic CLD and the recording of $1^{st}$ blood transfusion or drug abuse for viral CLD. These patients might have liver decompensation. In fact, the cause start was recorded in only 179 patients but in 6 other patients with Metavir F stage 0, the rate of Metavir F progression could be fixed at 0 by definition. However, the AOF could be measured in only 153 patients due to specimen fragmentation in 26 patients whereas the progression could not be fixed in the 6 patients with Metavir F stage 0 since baseline AOF is not null.

Population 2—

It included 157 patients with chronic hepatitis C between 1997 and 2002 detailed elsewhere (14). Mean inclusion age was 43.4±12.4 yr and 59.4% of patients were male.

Population 3—

It included 1056 patients with chronic hepatitis C, LB recruited in 9 French centers between 1997 and 2007 detailed elsewhere (15). Mean age was 45.4±12.5 yr at inclusion and 59.6% of patients were male.

Population 4—

It included 16 patients with various causes of CLD having two LB between 1997 and 2002 and different CLD causes.

Population 5—

It included 42 patients with chronic hepatitis C between 2004 and 2008. The blood tests were yearly measured for 2.4±0.5 yr.

Clinical Evaluation and Blood Tests

A full clinical examination was performed by a senior physician. The main clinical variables recorded were: inclusion age, start age, sex and CLD cause. Other variables are described elsewhere (14-16). Analyses of blood samples provided the usual variables as well as direct blood markers of fibrosis to calculate blood fibrosis tests. Thus, blood tests were calculated to estimate either fibrosis stage or AOF (14).

Liver Histological Assessment (Populations 1, 2 and 4)
Microscopic Analysis—

Biopsy specimens were fixed in a formalin-alcohol-acetic solution and embedded in paraffin; 5 µm thick sections were stained with hematoxylin-eosin-saffron and 0.1% picrosirius red solution. Fibrosis was staged by two independent pathologists, blinded for patient characteristics, according to the Metavir staging (6). The Metavir staging is also well adapted to the semi-quantitative evaluation of fibrosis in alcoholic CLD (17). In case of discrepancy, the specimens were re-examined under a double-headed microscope to reach a consensus.

Image Analysis—

AOF was measured on the same sections as the microscopic analysis using either a Leica Quantimet Q570 image processor as previously described from 1996 to 2006 (10) or an Aperio digital slide scanner (Scanscope® CS System, Aperio Technologies, Vista Calif. 92081, USA) image processor providing high quality images of 30,000×30,000 pixels and a resolution of 0.5 µm/pixel (magnification ×20) since 2007. A binary image (white and black) was obtained via an automatic thresholding technique using an algorithm developed in our laboratory.

Observers—

Overall there were 2 pathologists with 1 senior expert and 1 junior expert working in academic hospital. Image analysis was performed by the junior expert pathologist experienced in this technique (17) or by an engineer for the fully automated system.

Statistical Analysis

Quantitative variables were expressed as mean±SD, unless otherwise specified. The Pearson's rank correlation coefficient ($r_p$) was used for correlations between continuous variables or the Spearman correlation coefficient ($r_s$) when necessary. The Lowess regression by weighted least squares was used to determine the average trend of relationships between variables, mainly the progression course (18). The line rupture observed in these curves were checked by cut-offs determined according to maximum Youden index and diagnostic accuracy (data not shown). The curve shape was evaluated by corresponding test, e.g. quadratic trend test. To assess independent predictors, multiple linear regression for quantitative dependent variables, binary logistic regression for qualitative dependent variables and discriminant analysis for ordered variables were used with forward stepwise addition of variables. The prediction of each model is expressed by the adjusted $R^2$ coefficient ($_aR^2$) and/or by the diagnostic accuracy, i.e. true positives and negatives, respectively. An a risk<5% for a two-sided test was considered statistically significant. The statistical software used was SPSS version 11.5.1 (SPSS Inc., Chicago, Ill., USA).

Results

General Characteristics

The general characteristics of core populations 1 and 2 are presented in table 4. In population 1, variables at baseline (inclusion) were significantly different between alcoholic and viral causes, except for start age. Baseline variables were not significantly different between viral populations 1 and 2. It should be noted that the start age was similar between populations whereas the inclusion age was significantly older in alcoholic CLD which was responsible to a longer cause exposure.

Overall Description of Fibrosis Progression

Retrospective Measurement

Population 1—

Figure 9A:
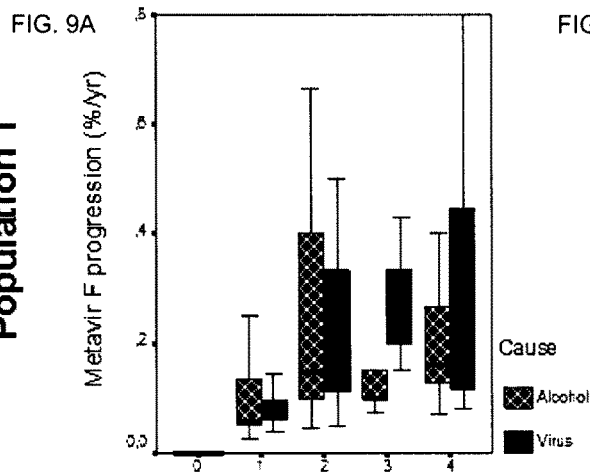
Figure 9B:
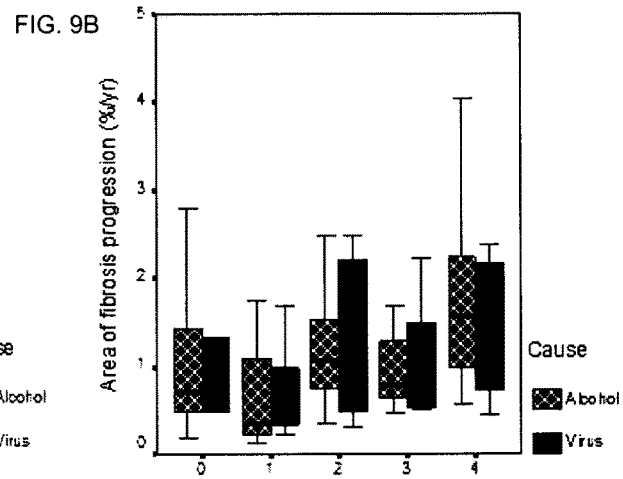

The progression, expressed in Metavir unit (MU) per year, ranged from 0 to 2.0 MU/yr for Metavir F (mean: 0.22±0.29, median: 0.13) and from 0.1 to 17.2%/yr for the AOF (mean: 1.8±2.6, median: 1.0). Both fibrosis progressions were highly correlated ($r_p$=0.90, p<$10^{-4}$, FIG. 8a). The fibrosis progression increased as a function of fibrosis F stage (FIGS. 9a and 9b). The AOF progression was significantly faster in alcoholic CLD than in viral CLD but not that of Metavir F (table 4).

Population 2—

Figure 9C:
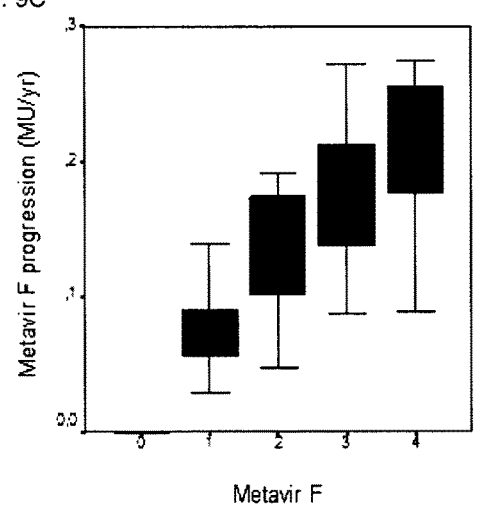
Figure 9D:
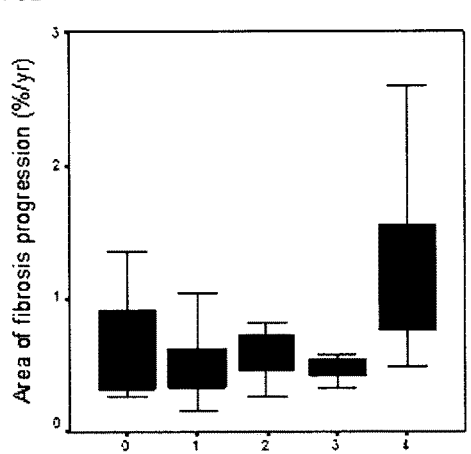
Figure 10A:
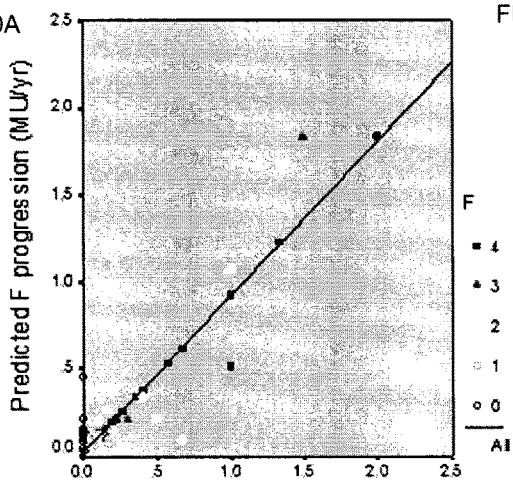
Figure 10B:
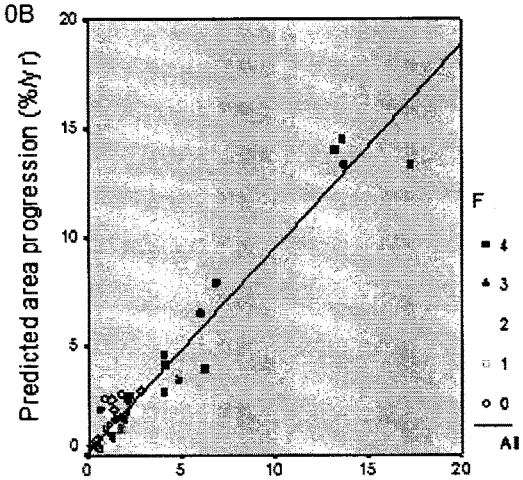
Figure 10C:
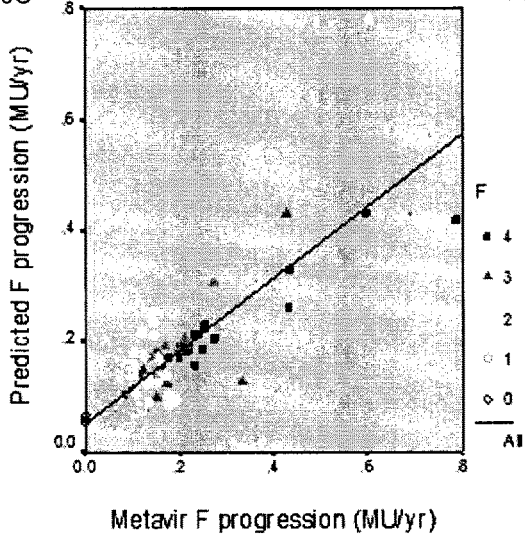
Figure 10D:
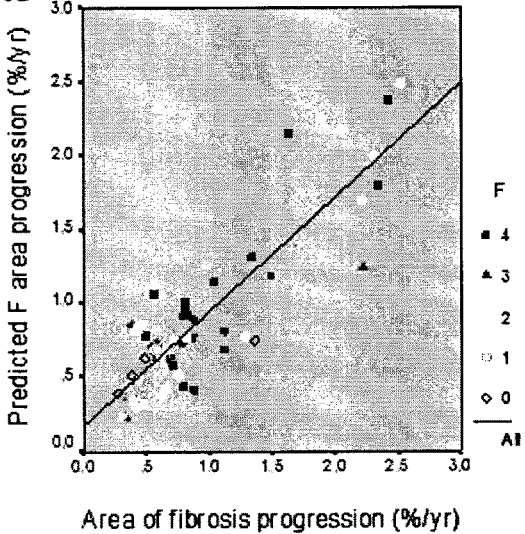

The rate of progression, expressed in Metavir unit (MU) per year, ranged from 0 to 0.8 MU/yr for Metavir F (mean: 0.16±0.14, median: 0.11) and from 0.2 to 4.5%/yr for the AOF (mean: 0.8±0.7, median: 0.6). AOF and F progressions were also well correlated $r_p$: 0.795 (p<$10^{-3}$) (FIG. 8b). The fibrosis progressions were significantly different according to F stage (ANOVA, p<$10^{-3}$) (FIGS. 9c and 9d). By Bonferroni post hoc comparison, the progressions were significantly different between each F stage for F progression (except between F2 and F3) but only in F4 vs F1 and F3 for AOF progression.

Comparison as a Function of Sex (Table 4)—

In alcoholic patients, F or AOF at inclusion were not significantly different between females and males, but cause duration was significantly shorter in females than in males. Consequently, the F or AOF progression was significantly faster in females than in males in alcoholic CLD. F or AOF at inclusion in population 2 were significantly higher in males than in females, but cause duration was not significantly different between males and females. Consequently, and conversely to alcoholic CLD, the F or AOF progression was significantly faster in males than in females in viral CLD (significant in more numerous population 2).

Comparison as a Function of Cause (Table 5)—

F and AOF progressions were dramatically and significantly increased in alcoholic CLD compared to viral CLD only in females.

Comparison Between Viral Populations—

The AOF progression were significantly higher in population 1 than in population 2 (table 4); this can be due to difference in AOF technique since AOF was significantly different or in populations since the F progression tended to be different.

Prospective Measurement

Population 4—

The mean interval between biopsies (follow-up duration) was 4.1±2.6 years. The yearly rate of progression was for Metavir F: mean: 0.17±0.27, median: 0.09 MU and for the area of fibrosis: mean: 1.3±3.4, median: 1.2%. These values were not significantly different than those estimated in population 1 (p=0.481 for F and p=0.567 for AOF).

Course of Fibrosis Progression

We described the average trends in course of fibrosis progression, as reflected by the plots of Lowess regression, according to three variables linked to times: cause duration, age at start cause and age at inclusion which is the sum of the two formers. Age at start cause was correlated with cause duration in population 1 ($r_p$=−0.449, p<$10^{-4}$), due to alcoholic CLD, but not in population 2 ($r_p$=−0.084 p=0.319). Particular trends in extremes of plots have to be cautiously interpreted since this could be due to a decreased robustness linked to fewer patients.

Cause Duration—

Figure 11A:
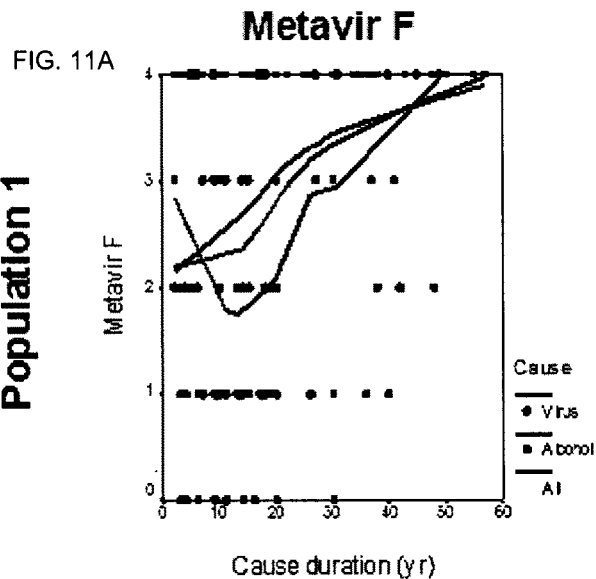
Figure 11B:
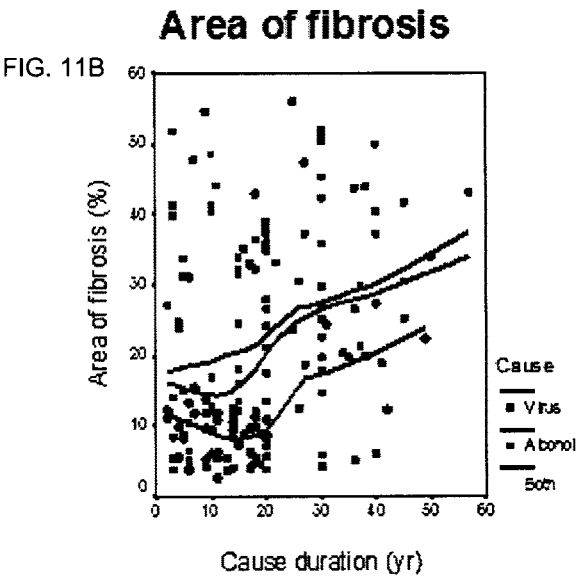
Figure 11C:
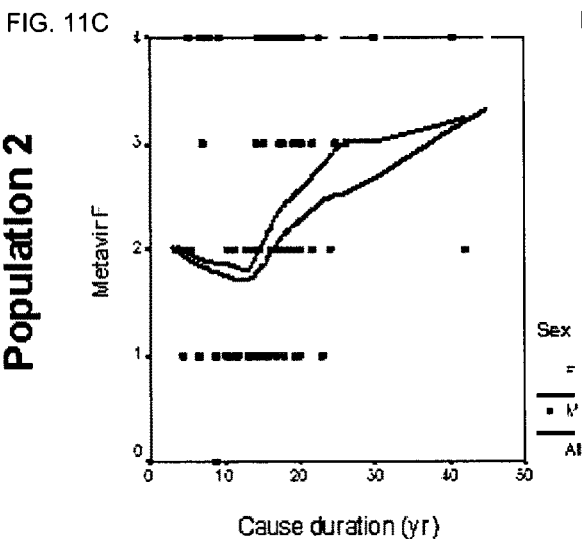
Figure 11D:
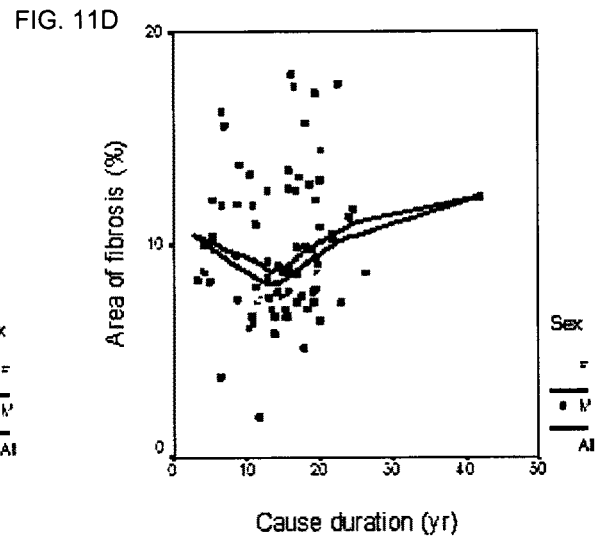

In population 1, the cause duration was weakly correlated with fibrosis level: F stage: $r_s$=0.357, p<$10^{-3}$ (FIG. 11a), AOF: $r_s$=0.316, p<$10^{-3}$ (FIG. 11b). In population 2, the cause duration was weakly correlated with F stage ($r_s$: 0.241, p=0.004) (FIG. 11c) or AOF ($r_s$: 0.201, p=0.018) with the same course in males and females (FIGS. 11c and 11d). All these figures show an unexpected decrease in the first 15 years and thereafter a progressive increase.

Start Age—

FIG. 12a shows that the F progression dramatically increased by 30-40 years of start age in alcoholic (≈40 years) and viral (≈30 years) CLD (population 1). The latter figure was confirmed in population 2 especially in men (FIG. 12c). This resulted in a progressive increase in F stage with start age in viral CLD (FIG. 13c) but this was not observed in alcoholic CLD (FIG. 13a) or in young patients with viral CLD (explanation below). However, the AOF progression displayed an almost linear increase over start age in alcoholic CLD whereas there was a plateau followed by a linear increase by ≈40 years of start age in viral CLD (population 1) (FIG. 12b). This was confirmed in population 2 especially in men (FIG. 12d). Globally, the AOF was relatively stable a function of start age in population 1 (FIG. 13b) and 2 (FIG. 13d). However, there were some peculiarities: a slow decrease in the first 20 years in males with viral CLD in F stages (FIG. 13c) or AOF (FIG. 13d) as well as a decrease by 40 yrs of start age in females (FIG. 13d).

Inclusion Age—

Figure 14A:
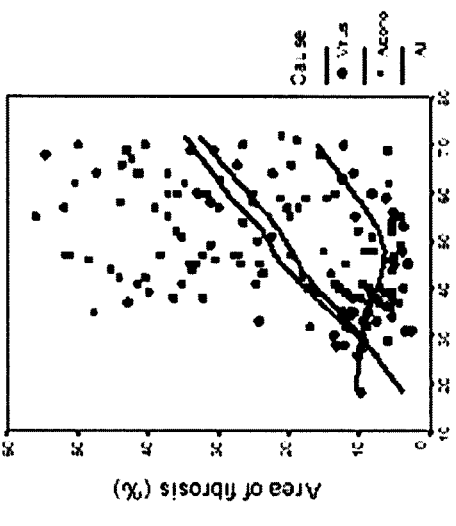
Figure 14B:
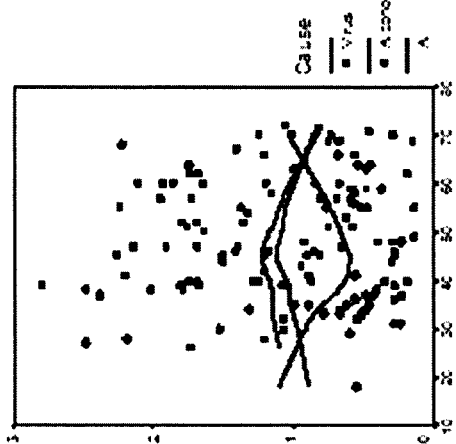
Figure 14C:
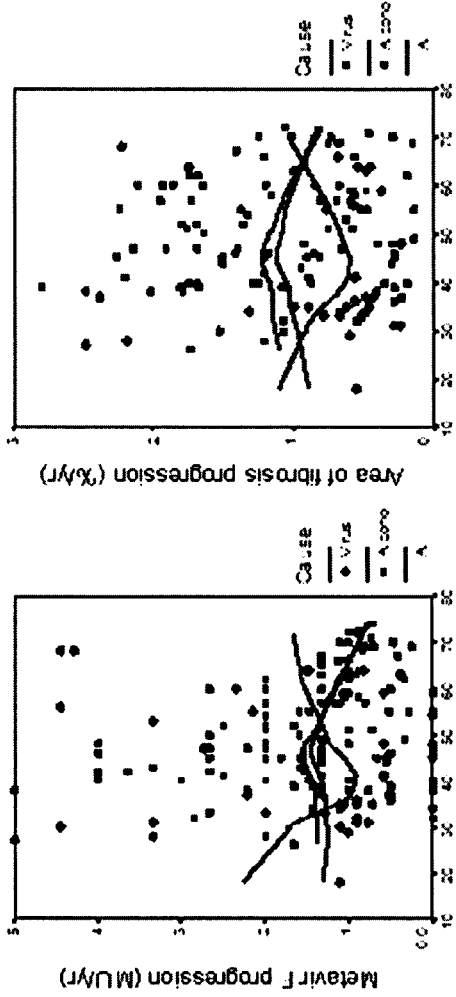
Figure 14D:
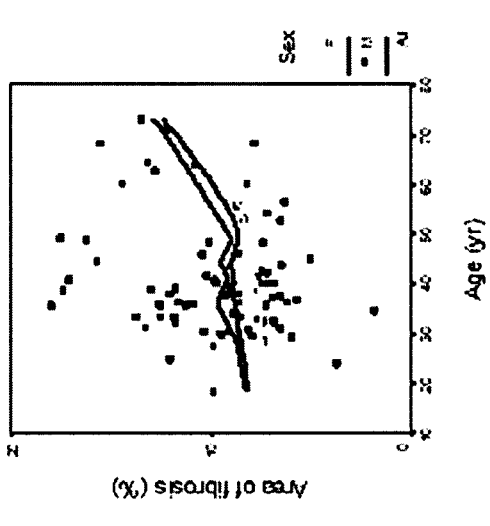
Figure 15A:
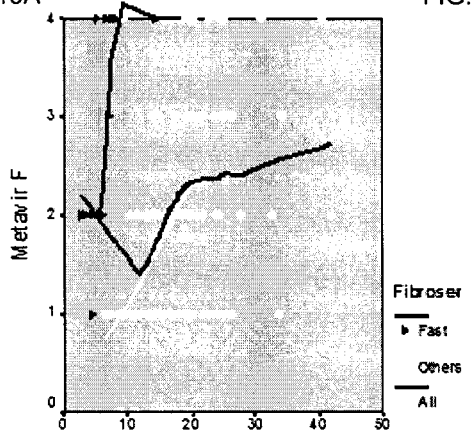
Figure 15B:
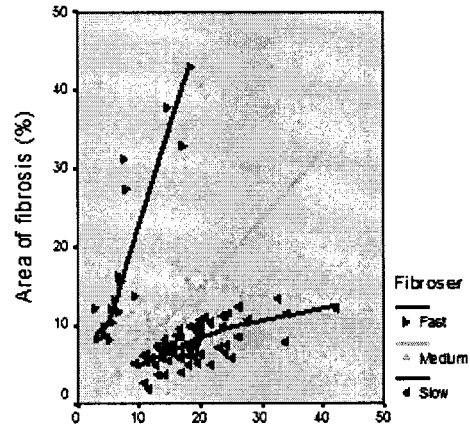
Figure 15C:
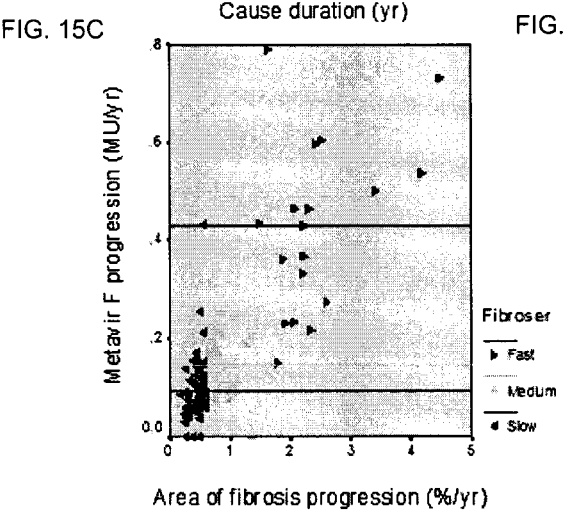
Figure 15D:
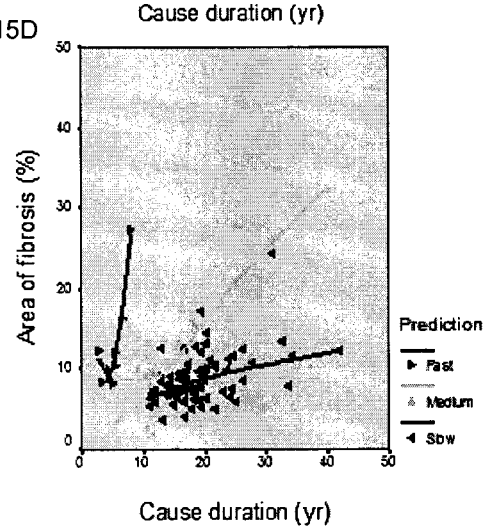

Considering F progression, in alcoholic CLD there was a stable progression until 50 yr (FIG. 14a) then a decrease whereas in viral CLD after an initial decrease below 35 yr, especially in men, there was thereafter an increase (FIGS. 14a and 14d). Considering F level, the increase was linear with age in alcoholic CLD and occurred by 40-50 yr in viral CLD (FIG. 15a). Populations 2 and 3 stated that this increase occurred by age 40 yr in males and 50 yr in females in viral CLD (FIGS. 15b and 15c). There was an initial F decline in viral CLD (FIG. 15a), especially in men (FIG. 15b) which was not confirmed in population 3 (FIG. 15c) but there were less young patients in this latter population (as reflected by an older age: p=0.06).

Figure 14E:
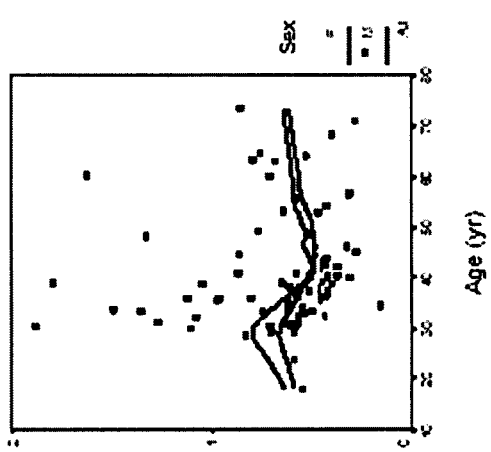
Figure 14F:
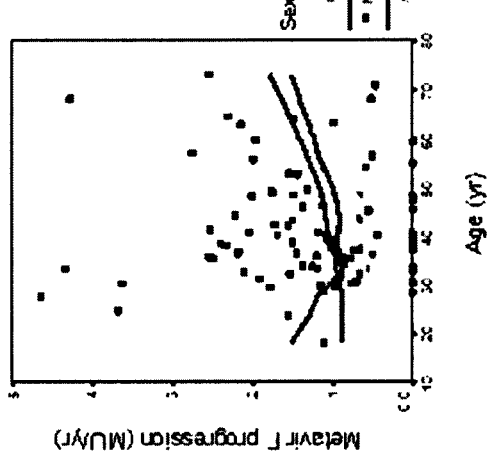

AOF progression did not depend on the inclusion age in alcoholic CLD (FIG. 14b) whereas there was a late increase in viral CLD (FIGS. 14b and 14e). Consequently, the AOF level linearly increased with age in alcoholic CLD (FIG. 14c) whereas this occurred by age 50 yr in viral CLD (FIG. 14f).

Sex—

We state here the particular relationship between sexes and CLD cause since sex effect has been already mentioned in viral CLD. Whereas there was a global parallelism between males and females in viral CLD, females in alcoholic CLD had two particularities: a slowdown between 30-50 yr and a late increase in fibrosis progression and level by 50 yr of start age (data not shown). The same differences were observed for inclusion age at the difference that the slowdown was observed later between 45-50 yr, as expected.

Times to Cirrhosis

In population 1, times to cirrhosis was $24.7\pm13.3$ yr in alcoholic CLD vs $22.1\pm15.9$ yr in viral CLD (p=0.495) and $28.0\pm12.5$ yr in males vs $16.1\pm11.4$ yr (p=0.001) in females in alcoholic CLD. In (viral) population 2, it was $17.0\pm8.0$ yr in males vs $24.0\pm10.0$ yr (p=0.017) in females.

Non Invasive Evaluation observed FibroMeter™ progression [(FibroMeter™ t2−FibroMeter™ t1)/(t2−t1)] was $0.049\pm0.058$/yr in population 5 whereas the estimated FibroMeter™ progression (FibroMeter™ t2/cause duration) was $0.038\pm0.033$/yr in population 2 (p=0.217).

Identifying Categories of Fibrosers

In population 2, it was possible to distinguish three categories of fibrosers as a function of AOF progression (FIG. 15b) rather on F progression (FIG. 15a). The cut-offs were 0.58 and 1.36%/yr distinguishing slow (52.5%), medium (34.5%) and fast (12.9%) fibrosers where AOF progression was: $0.42\pm0.10$, $0.81\pm0.21$ and $2.43\pm0.81$%/yr ($p<10^{-3}$), respectively. Fibrosers, defined by AOF progression, were in agreement with F progression: $0.09\pm0.06$, $0.15\pm0.06$ and $0.43\pm0.18$ MU/yr ($p<10^{-3}$), respectively slow, medium and fast fibrosers (FIG. 15c). The start age increased with fibroser degree: $25.2\pm10.5$, $28.7\pm10.8$ and $33.0\pm13.6$ yr, respectively ($p<10^{-3}$). The proportion of males increased with fibroser degree: 53.4%, 66.7% and 77.8%, respectively (p=0.034). By stepwise discriminant analysis, fibrosers were predicted by Metavir F, AOF, F progression and cause duration (diagnostic accuracy: 91.4%). The fast fibrosers were predicted by increased AOF, younger inclusion age and older start age with diagnostic accuracy: 100.0% by stepwise binary logistic regression.

TABLE 2

Fibrosis evaluation

| Fibrosis evaluation | | | Fibrosis progression | | |
|---|---|---|---|---|---|
| Method | Technique | Calculation[a] | Description | Advantages | Limits |
| Single biopsy measurement | 1 biopsy | FL/cause duration | Transversal (retrospective) measurement | Availability+ | Linearity Start estimation |
| Repeated biopsy measurement | 2 biopsies | (FLt2-FLt1)/ (t2-t1) | Longitudinal (prospective) measurement | Precision Reference | Variability Unavailability Short duration |
| Single non-invasive test estimation | 1 test[b] | FL/cause duration | Transversal (retrospective) estimation | Availability++ | Linearity Start estimation |
| Repeated non-invasive test estimation | 2 tests | (FLt2-FLt1)/ (t2-t1) | Longitudinal (prospective) estimation | Precision Repeatability | |

[a]FL is the fibrosis level and t is the corresponding date
[b]Non-invasive (blood test in the present study)

TABLE 3

Main characteristics of different populations used in this study.

| Population | Cause | Patients (n) | Fibrosis evaluation | Area of fibrosis[a] | Duration Time | Fibrosis progression |
|---|---|---|---|---|---|---|
| 1 | Alcohol virus | 185 | 1 LB, 1 blood test | Yes | Cause duration[b] | Retrospective measurement + estimation |
| 2 | Virus | 157 | 1 LB, 1 blood test | Yes | Cause duration[b] | Retrospective measurement + estimation |
| 3 | Virus | 1056 | 1 LB, 1 blood test | No | No | Retrospective measurement + estimation[c] |
| 4 | Miscellaneous | 16 | 2 LB | Yes | Follow-up | Prospective measurement |
| 5 | Virus | 42 | 0 LB, 2 blood tests | No | Follow-up | Prospective estimation |

[a]On LB;
[b]Cause duration = time between age at inclusion when liver fibrosis level was measured and age at the start of the liver disease;
[c]Limited to the plot fibrosis level vs age.

TABLE 4

Clinical characteristics of populations 1 and 2.

| Cause | Population 1 Alcohol | Population 1 Virus | $p^a$ | Population 2 Both | Population 2 Virus | $p^b$ |
|---|---|---|---|---|---|---|
| N | 136 | 49 | — | 185 | 157 | — |
| Age at inclusion (yr) | 49.9 ± 11.2 | 44.2 ± 14.6 | 0.02 | 48.5 ± 12.3 | 43.4 ± 12.4 | 0.793 |
| Age at cause start (yr) | 28.8 ± 9.5 | 28.2 ± 13.5 | 0.779 | 28.8 ± 10.8 | 27.4 ± 11.2 | 0.707 |
| Cause duration (yr) | 21.3 ± 13.2 | 15.8 ± 10.7 | 0.006 | 19.8 ± 12.9 | 16.5 ± 7.3 | 0.604 |
| Sex (% M) | 72.8 | 53.1 | 0.011 | 67.6 | 59.4 | 0.550 |
| Cause (% virus) | — | — | — | 26.5 | 100 | — |
| Metavir F (%): | | | 0.002 | | | — |
| 0 | 9.6 | 10.2 | | 9.7 | 10.3 | 0.998 |
| 1 | 14.0 | 32.7 | | 18.9 | 33.5 | 0.886 |
| 2 | 13.2 | 20.4 | | 15.1 | 25.8 | 0.419 |
| 3 | 6.6 | 12.2 | | 8.1 | 11.0 | 0.303 |
| 4 | 56.6 | 24.5 | | 48.1 | 19.4 | 0.414 |
| Area of fibrosis (%) | 23.5 ± 14.7 | 13.6 ± 11.7 | $<10^{-3}$ | 20.7 ± 14.6 | 10.7 ± 6.5 | 0.005 |
| Complication (%) | 29.4 | 0 | $<10^{-3}$ | 21.6 | 0 | — |
| Progression rate: | | | | | | |
| Metavir F (MU/yr) | 0.23 ± 0.32 | 0.19 ± 0.21 | 0.424 | 0.22 ± 0.29 | 0.16 ± 014 | 0.120 |
| Area of fibrosis (%/yr) | 2.0 ± 2.9 | 1.3 ± 1.4 | 0.027 | 1.8 ± 2.6 | 0.8 ± 0.7 | 0.017 |

[a] alcohol vs virus;
[b] vs viral population 1
NA: not available

TABLE 5

Fibrosis: data at inclusion and course as a function of sex in populations 1 and 2.

| | MALES | FEMALES | $P^A$ |
|---|---|---|---|
| POPULATION 1 | | | |
| AGE AT CAUSE START (YR) | | | |
| ALCOHOL | 26.9 ± 8.1 | 34.1 ± 11.0 | 0.001 |
| VIRUS | 27.5 ± 15.0 | 29.0 ± 11.7 | 0.337 |
| P | 0.354 | 0.160 | — |
| BOTH | 27.0 ± 9.9 | 32.2 ± 11.5 | 0.001 |
| AGE AT INCLUSION (YR) | | | |
| ALCOHOL | 50.6 ± 12.0 | 48.0 ± 8.4 | 0.358 |
| VIRUS | 42.2 ± 15.1 | 46.7 ± 13.6 | 0.400 |
| P | 0.001 | 0.680 | — |
| BOTH | 48.8 ± 13.1 | 47.5 ± 10.7 | 0.623 |
| CAUSE DURATION (YR) | | | |
| ALCOHOL | 23.9 ± 13.1 | 14.2 ± 11.0 | $<10^{-3}$ |
| VIRUS | 14.6 ± 9.3 | 17.2 ± 12.2 | 0.626 |
| P | 0.001 | 0.287 | — |
| BOTH | 22.0 ± 12.9 | 15.3 ± 11.4 | 0.001 |
| METAVIR F SCORE | | | |
| ALCOHOL | 2.8 ± 1.5 | 2.9 ± 1.4 | 0.724 |
| VIRUS | 2.1 ± 1.3 | 2.1 ± 1.4 | 0.984 |
| P | 0.012 | 0.024 | — |
| BOTH | 2.7 ± 1.5 | 2.6 ± 1.5 | 0.737 |
| F PROGRESSION (MU/YR) | | | |
| ALCOHOL | 0.17 ± 0.23 | 0.41 ± 0.43 | $<10^{-3}$ |
| VIRUS | 0.20 ± 0.21 | 0.18 ± 0.22 | 0.609 |
| $P^A$ | 0.685 | 0.019 | — |
| BOTH | 0.17 ± 0.23 | 0.32 ± 0.38 | 0.011 |
| AREA OF FIBROSIS (%) | | | |
| ALCOHOL | 22.9 ± 14.7 | 25.0 ± 14.8 | 0.483 |
| VIRUS | 14.3 ± 11.9 | 12.2 ± 11.4 | 0.199 |
| P | 0.014 | 0.001 | — |
| BOTH | 20.8 ± 14.5 | 20.2 ± 14.9 | 0.636 |
| AOF PROGRESSION (%/YR) | | | |
| ALCOHOL | 1.4 ± 1.8 | 3.5 ± 4.2 | 0.001 |
| VIRUS | 1.4 ± 1.4 | 1.1 ± 1.4 | 0.146 |
| P | 0.762 | 0.001 | — |
| BOTH | 1.4 ± 1.7 | 2.7 ± 3.6 | 0.106 |
| POPULATION 2 | | | |
| AGE AT CAUSE START (YR) | 26.1 ± 10.9 | 29.4 ± 11.4 | 0.021 |
| AGE AT INCLUSION (YR) | 41.8 ± 11.8 | 47.1 ± 13.1 | 0.015 |
| CAUSE DURATION (YR) | 15.7 ± 6.8 | 17.7 ± 8.0 | 0.195 |
| METAVIR F SCORE | 2.3 ± 1.2 | 1.9 ± 1.2 | 0.030 |
| F PROGRESSION (MU/YR) | 0.18 ± 0.14 | 0.13 ± 0.13 | 0.004 |
| AREA OF FIBROSIS (%) | 11.4 ± 6.9 | 9.6 ± 5.8 | 0.018 |
| AOF PROGRESSION (%/YR) | 0.91 ± 0.74 | 0.67 ± 0.67 | 0.004 |
| COMPARISON VIRAL POPULATIONS 1 AND 2 (P): | | | |
| AGE AT CAUSE START (YR) | 0.665 | 0.888 | — |
| AGE AT INCLUSION (YR) | 0.903 | 0.903 | — |
| CAUSE DURATION (YR) | 0.516 | 0.830 | — |
| METAVIR F SCORE | 0.473 | 0.549 | — |
| F PROGRESSION | 0.659 | 0.311 | — |
| AREA OF FIBROSIS (%) | 0.274 | 0.301 | — |
| AOF PROGRESSION | 0.095 | 0.213 | — |

[A] Mann Whitney test

REFERENCES

References of Example 1

1. Oberti F, Valsesia E, Pilette C, Rousselet M C, Bedossa P, Aube C, Gallois Y, et al. Noninvasive diagnosis of hepatic fibrosis or cirrhosis. *Gastroenterology*, 1997; 113:1609-1616.
2. Poynard T, Aubert A, Bedossa P, Abella A, Naveau S, Paraf F, Chaput J C. A simple biological index for detection of alcoholic liver disease in drinkers. *Gastroenterology* 1991; 100:1397-1402.
3. Naveau S, Poynard T, Benattar C, Bedossa P, Chaput J C. Alpha-2-macroglobulin and hepatic fibrosis. Diagnostic interest. *Dig Dis. Sci.* 1994; 39:2426-2432.
4. Wai C T, Greenson J K, Fontana R I, Kalbfleisch J D, Marrero J A, Conjeevaram H S, Lok A S. A simple noninvasive index can predict both significant fibrosis and cirrhosis in patients with chronic hepatitis C. *Hepatology* 2003; 38:518-526.
5. Cales P, Boursier J, Oberti F, Hubert I, Gallois Y, Rousselet M C, Dib N, et al. FibroMeters™: a family of blood tests for liver fibrosis. *Gastroenterol Clin Biol.* 2008; 32:40-51.
6. Adams L A, Bulsara M, Rossi E, DeBoer B, Speers D, George J, Kench J, et al. Hepascore: an accurate validated predictor of liver fibrosis in chronic hepatitis C infection. *Clin Chem.* 2005; 51:1867-1873.

7. Intraobserver and interobserver variations in liver biopsy interpretation in patients with chronic hepatitis C. The French METAVIR Cooperative Study Group. *Hepatology* 1994; 20:15-20.
8. Michalak S, Rousselet M C, Bedossa P, Pilette C, Chappard D, Oberti F, Gallois Y, et al. Respective roles of porto-septal fibrosis and centrilobular fibrosis in alcoholic liver disease. *J. Pathol.* 2003; 201:55-62.
9. Pilette C, Rousselet M C, Bedossa P, Chappard D, Oberti F, Rifflet H, Maiga M Y, et al. Histopathological evaluation of liver fibrosis: quantitative image analysis vs semiquantitative scores. Comparison with serum markers. *J. Hepatol.* 1998; 28:439-446.
10. Moal F, Chappard D, Wang J, Vuillemin E, Michalak-Provost S, Rousselet M C, Oberti F, et al. Fractal dimension can distinguish models and pharmacologic changes in liver fibrosis in rats. *Hepatology,* 2002; 36:840-849.

References of Example 2

1. Ascione A, Tartaglione T, Giuseppe Di Costanzo G. Natural history of chronic hepatitis C virus infection. Dig Liver Dis 2007; 39 Suppl 1:S4-7.
2. Feld J J, Liang T J. Hepatitis C—identifying patients with progressive liver injury. Hepatology 2006; 43:S194-206.
3. Lawson A, Ryder S D. Progression of hepatic fibrosis in chronic hepatitis C and the need for treatment in mild disease. Eur J Gastroenterol Hepatol 2006; 18:343-347.
4. Rodriguez-Torres M, Rodriguez-Orengo J F, Rios-Bedoya C F, Fernandez-Carbia A, Marxuach-Cuetara A M, Lopez-Tones A, Jimenez-Rivera J. Effect of hepatitis C virus treatment in fibrosis progression rate (FPR) and time to cirrhosis (TTC) in patients co-infected with human immunodeficiency virus: a paired liver biopsy study. J Hepatol 2007; 46:613-619.
5. Albanis E, Friedman S L. Antifibrotic agents for liver disease. Am J Transplant 2006; 6:12-19.
6. Intraobserver and interobserver variations in liver biopsy interpretation in patients with chronic hepatitis C. The French METAVIR Cooperative Study Group. Hepatology 1994; 20:15-20.
7. Ishak K, Baptista A, Bianchi L, Callea F, De Groote J, Gudat F, Denk H, et al. Histological grading and staging of chronic hepatitis. J Hepatol 1995; 22:696-699.
8. Winkfield B, Aube C, Burtin P, Cales P. Inter-observer and intra-observer variability in hepatology. Eur J Gastroenterol Hepatol 2003; 15:959-966.
9. Nagula S, Jain D, Groszmann R J, Garcia-Tsao G. Histological-hemodynamic correlation in cirrhosis—a histological classification of the severity of cirrhosis. J Hepatol 2006; 44:111-117.
10. Pilette C, Rousselet M C, Bedossa P, Chappard D, Oberti F, Rifflet H, Maiga M Y, et al. Histopathological evaluation of liver fibrosis: quantitative image analysis vs semiquantitative scores. Comparison with serum markers. J Hepatol 1998; 28:439-446.
11. Pol S, Carnot F, Nalpas B, Lagneau J L, Fontaine H, Serpaggi J, Serfaty L, et al. Reversibility of hepatitis C virus-related cirrhosis. Hum Pathol 2004; 35:107-112.
12. Goodman Z D, Becker R L, Jr., Pockros P J, Afdhal N H. Progression of fibrosis in advanced chronic hepatitis C: evaluation by morphometric image analysis. Hepatology 2007; 45:886-894.
13. Levine R A, Sanderson S O, Ploutz-Snyder R, Murray F, Kay E, Hegarty J, Nolan N, et al. Assessment of fibrosis progression in untreated Irish women with chronic hepatitis C contracted from immunoglobulin anti-D. Clin Gastroenterol Hepatol 2006; 4:1271-1277.
14. Cales P, Oberti F, Michalak S, Hubert-Fouchard I, Rousselet M C, Konate A, Gallois Y, et al. A novel panel of blood markers to assess the degree of liver fibrosis. Hepatology 2005; 42:1373-1381.
15. Cales P, de Ledinghen V, Halfon P, Bacq Y, Leroy V, Boursier J, Foucher J, et al. Evaluating the accuracy and increasing the reliable diagnosis rate of blood tests for liver fibrosis in chronic hepatitis C. Liver Int 2008; 28:1352-1362.
16. Oberti F, Valsesia E, Pilette C, Rousselet M C, Bedossa P, Aube C, Gallois Y, et al. Noninvasive diagnosis of hepatic fibrosis or cirrhosis. Gastroenterology 1997; 113: 1609-1616.
17. Michalak S, Rousselet M C, Bedossa P, Pilette C, Chappard D, Oberti F, Gallois Y, et al. Respective roles of porto-septal fibrosis and centrilobular fibrosis in alcoholic liver disease. J Pathol 2003; 201:55-62.
18. Hubert J B, Burgard M, Dussaix E, Tamalet C, Deveau C, Le Chenadec J, Chaix M L, et al. Natural history of serum HIV-1 RNA levels in 330 patients with a known date of infection. The SEROCO Study Group. Aids 2000; 14:123-131.
19. Kage M, Shimamatu K, Nakashima E, Kojiro M, Inoue O, Yano M. Long-term evolution of fibrosis from chronic hepatitis to cirrhosis in patients with hepatitis C: morphometric analysis of repeated biopsies. Hepatology 1997; 25:1028-1031.
20. Boursier J, Chaigneau J, Roullier V, Laine F, Michalak S, Hubert I, Dib N, et al. Histological and non-invasive quantitation of liver steatosis. J Hepatol 2009; 50: 5357.
21. Poynard T, Mathurin P, Lai C L, Guyader D, Poupon R, Tainturier M H, Myers R P, et al. A comparison of fibrosis progression in chronic liver diseases. J Hepatol 2003; 38:257-265.
22. Poynard T, Ratziu V, Charlotte F, Goodman Z, McHutchison J, Albrecht J. Rates and risk factors of liver fibrosis progression in patients with chronic hepatitis c. J Hepatol 2001; 34:730-739.
23. Deuffic-Burban S, Poynard T, Valleron A J. Quantification of fibrosis progression in patients with chronic hepatitis C using a Markov model. J Viral Hepat 2002; 9:114-122.
24. Poynard T, Bedossa P, Opolon P. Natural history of liver fibrosis progression in patients with chronic hepatitis C. The OBSVIRC, METAVIR, CLINIVIR, and DOSVIRC groups. Lancet 1997; 349:825-832.
25. Sobesky R, Mathurin P, Charlotte F, Moussalli J, Olivi M, Vidaud M, Ratziu V, et al. Modeling the impact of interferon alfa treatment on liver fibrosis progression in chronic hepatitis C: a dynamic view. The Multivirc Group. Gastroenterology 1999; 116:378-386.

Although the present invention has been described hereinabove by way of preferred embodiments thereof, it can be modified, without departing from the spirit and nature of the subject invention as defined in the appended claims.

The invention claimed is:

1. A method for treating an individual suffering from liver fibrosis determined to be a fast fibroser, said method comprising:
  determining an individual to be a fast fibroser by assessing the fibrosis progression in said individual, by
    measuring at least three markers in the individual, wherein said markers are measured in a blood sample obtained from the individual and are selected from the group consisting of α-2 macroglobulin, hyaluronic acid, gamma-glutamyl transpeptidase, bilirubin, platelet count, prothrombin index, aspartate amino-transferase, alanine amino-transferase, urea, glycemia, and ferritin; and/or said markers are clinical markers selected from weight, age and sex; combining said at least three measured markers in a logistic or linear regression function, thereby determining a fibrosis level in the individual; and calculating a ratio of said fibrosis level to cause duration, thereby obtaining a value useful for assessing the liver fibrosis progression in the individual;

treating the individual suffering from liver fibrosis determined to be a fast fibroser by administering without delay to said individual at least one therapeutic agent, wherein the at least one therapeutic agent is an antifibrotic agent or an agent for treating the underlying cause responsible for liver fibrosis, said underlying cause responsible for liver fibrosis being a viral infection, excessive alcohol consumption, or a non-alcoholic fatty liver disease (NAFLD).

2. The method of claim 1, wherein fibrosis progression is assessed by measuring at two different times t1 and t2 the fibrosis levels FL(t1) and FL(t2); and calculating a ratio FL(t2)−FL(t1) to cause duration, wherein cause duration is defined as (t2−t1).

3. The method according to claim 1, wherein the at least one therapeutic agent is an antifibrotic agent selected from the group consisting of simtuzumab, GR-MD-02, stem cell transplantation, *Phyllanthus urinaria*, Fuzheng Huayu, S-adenosyl-L-methionine, S-nitrosol-N-acetylcystein, silymarin, phosphatidylcholine, N-acetylcysteine, resveratrol, vitamin E, losartan, telmisartan, naltrexone, RF260330, sorafenib, gleevec, nilotinib, INT747, FG-3019, oltipraz, pirfenidone, halofuginone, polaorezin, gliotoxin, sulfasalazine, rimonabant and combinations thereof.

4. The method according to claim 1, wherein the at least one therapeutic agent is an agent for treating the underlying cause responsible for liver fibrosis, said underlying cause responsible for liver fibrosis being a viral infection, and wherein the agent is selected from the group consisting of interferon, pegylated interferon 2b (peginterferon 2b), infliximab, ribavirin, boceprevir, telaprevir, simeprevir, sofosbuvir, daclatasvir, elbasvir, grazoprevir, velpatasvir, lamivudine, adefovir dipivoxil, entecavir, telbivudine, tenofovir, clevudine, ANA380, zadaxin, CMX 157, ARB-1467, ARB-1740, ALN-HBV, BB-HB-331, Lunar-HBV, ARO-HBV, Myrcludex B, GLS4, NVR 3-778, AIC 649, JNJ56136379, ABI-H0731, AB-423, REP 2139, REP 2165, GSK3228836, GSK33389404, RNaseH Inhibitor, GS 4774, INO-1800, HB-110, TG1050, HepTcell, TomegaVax HBV, RG7795, SB9200, EYP001, CPI 431-32 and combinations thereof.

5. The method according to claim 1, wherein the at least one therapeutic agent is an agent for treating the underlying cause responsible for liver fibrosis, said underlying cause responsible for liver fibrosis being excessive alcohol consumption, and wherein the agent is selected from the group consisting of topiramate, disulfiram, naltrexone, acamprosate and baclofen.

6. The method according to claim 1, wherein the at least one therapeutic agent is an agent for treating the underlying cause responsible for liver fibrosis, said underlying cause responsible for liver fibrosis being a non-alcoholic fatty liver disease (NAFLD), and wherein the agent is selected from the group consisting of orlistat, metformin, pioglitazone, atorvastatin, ezetimine, vitamin E, sylimarine, pentoxyfylline, ARBs, EPL, EPA-E, a multistrain biotic comprising *L. rhamnosus* and *L. bulgaricus*, simtuzumab, obeticholic acid, elafribanor (GFT505), DUR-928, GR-MD, 02, aramchol, RG-125, cenicriviroc (CVC) and combinations thereof.

7. A method for treating an individual suffering from liver fibrosis determined to be a fast fibroser, said method comprising:

determining an individual to be a fast fibroser by assessing the fibrosis progression in said individual, by measuring in a sample of the individual at least one variable or score further defined as:

biological variables further defined as α-2 macroglobulin (α2M), Hyaluronic acid (HA), Apolipoprotein A1 (ApoA1), Type III procollagen N-terminal propeptide (P3P), γ-glutamyl transpeptidase (GGT), bilirubin, β-globulin, γ-globulin (GLB), Platelets (PLT), Prothrombin time (PT), Prothrombin index (PI), Aspartate aminotransferase (AST), Alanine aminotransferase (ALT), Urea, Sodium (NA), Glycemia, Triglycerides, Albumin (ALB), Alkaline phosphatase (ALP), Human cartilage glycoprotein 39 (YKL-40), Tissue inhibitor of matrix metalloproteinase 1 (TIMP-1), Matrix metalloproteinase 2 (MMP-2), Ferritin, TGFβ1, Laminin, βγ-block, Haptoglobin, C-Reactive protein (CRP), and/or cholesterol;

complex biological variable;

clinical variables further defined as age at first contact, age, cause duration, firm liver, splenomegaly, ascites, collateral circulation, cause of CLD, and/or esophageal varices (EV grade);

score further defined as Metavir F stage, Area of fibrosis (AOF), fractal dimension, Fibrosis score, PGA score, PGAA score, Hepascore, Aspartate-aminotransferase to platelet ratio index (APRI), and/or European Liver Fibrosis (ELF), and/or combinations thereof; and combining the selected variables in a mathematical function, further defined as a multiple linear regression function, a non-linear regression function, or simple mathematic function;

treating the individual suffering from liver fibrosis determined to be a fast fibroser by administering without delay to said individual at least one therapeutic agent, wherein the at least one therapeutic agent is an antifibrotic agent or an agent for treating the underlying cause responsible for liver fibrosis, said underlying cause responsible for liver fibrosis being a viral infection, excessive alcohol consumption, or a non-alcoholic fatty liver disease (NAFLD).

8. The method according to claim 7, wherein the at least one therapeutic agent is an antifibrotic agent selected from the group consisting of simtuzumab, GR-MD-02, stem cell transplantation, *Phyllanthus urinaria*, Fuzheng Huayu, S-adenosyl-L-methionine, S-nitrosol-N-acetylcystein, silymarin, phosphatidylcholine, N-acetylcysteine, resveratrol, vitamin E, losartan, telmisartan, naltrexone, RF260330, sorafenib, gleevec, nilotinib, INT747, FG-3019, oltipraz, pirfenidone, halofuginone, polaorezin, gliotoxin, sulfasalazine, rimonabant and combinations thereof.

9. The method according to claim 7, wherein the at least one therapeutic agent is an agent for treating the underlying cause responsible for liver fibrosis, said underlying cause responsible for liver fibrosis being a viral infection, and wherein the agent is selected from the group consisting of interferon, pegylated interferon 2b (peginterferon 2b), infliximab, ribavirin, boceprevir, telaprevir, simeprevir, sofosbuvir, daclatasvir, elbasvir, grazoprevir, velpatasvir, lamivudine, adefovir dipivoxil, entecavir, telbivudine, tenofovir, clevudine, ANA380, zadaxin, CMX 157, ARB-1467, ARB-1740, ALN-HBV, BB-HB-331, Lunar-HBV, ARO-HBV, Myrcludex B, GLS4, NVR 3-778, AIC 649, JNJ56136379, ABI-H0731, AB-423, REP 2139, REP 2165, GSK3228836, GSK33389404, RNaseH Inhibitor, GS 4774, INO-1800, HB-110, TG1050, HepTcell, TomegaVax HBV, RG7795, SB9200, EYP001, CPI 431-32 and combinations thereof.

10. The method according to claim 7, wherein the at least one therapeutic agent is an agent for treating the underlying cause responsible for liver fibrosis, said underlying cause responsible for liver fibrosis being excessive alcohol consumption, and wherein the agent is selected from the group consisting of topiramate, disulfiram, naltrexone, acamprosate and baclofen.

11. The method according to claim 7, wherein the at least one therapeutic agent is an agent for treating the underlying cause responsible for liver fibrosis, said underlying cause responsible for liver fibrosis being a non-alcoholic fatty liver disease (NAFLD), and wherein the agent is selected from the group consisting of orlistat, metformin, pioglitazone, atorvastatin, ezetimine, vitamin E, sylimarine, pentoxyfylline, ARBs, EPL, EPA-E, a multistrain biotic comprising *L. rhamnosus* and *L. bulgaricus*, simtuzumab, obeticholic acid, elafribanor (GFT505), DUR-928, GR-MD, 02, aramchol, RG-125, cenicriviroc (CVC) and combinations thereof.

* * * * *